United States Patent [19]

Nakane

[11] Patent Number: 4,735,962

[45] Date of Patent: Apr. 5, 1988

[54] 7-THIABICYCLOHEPTANE SUBSTITUTED DIAMIDE AND ITS CONGENER PROSTAGLANDIN ANALOGS

[75] Inventor: Masami Nakane, Aichi, Japan

[73] Assignee: E. R. Squibb & Sons, Inc., Princeton, N.J.

[21] Appl. No.: 916,083

[22] Filed: Oct. 6, 1986

[51] Int. Cl.$^4$ .................. C07D 409/06; C07D 333/78; A01K 31/38; A01K 31/41
[52] U.S. Cl. ..................................... 514/382; 514/443; 548/253; 549/59
[58] Field of Search ........................... 549/59; 548/253; 514/382, 443

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |
| 4,588,741 | 5/1986 | Nakane | 514/443 |
| 4,588,742 | 5/1986 | Nakane | 514/443 |
| 4,595,692 | 6/1986 | Nakane | 514/443 |
| 4,638,012 | 1/1987 | Nakane | 514/469 |
| 4,639,461 | 1/1987 | Nakane | 514/382 |
| 4,647,573 | 3/1987 | Nakane | 514/382 |
| 4,652,576 | 3/1987 | Nakane | 514/382 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

Primary Examiner—Robert Gerstl
Attorney, Agent, or Firm—Lawrence S. Levinson; Burton Rodney

[57] ABSTRACT

7-Thiabicycloheptane substituted diamide and congener prostaglandin analogs are provided having the structural formula

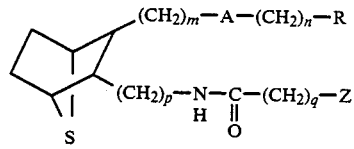

wherein m is 1 to 4; A is —CH=CH— or —CH$_2$—CH$_2$—; n is 1 to 5; R is $CO_2H$, $CO_2$alkyl, $CO_2$alkali metal, $CO_2$polyhydroxyamine salt, —$CH_2OH$,

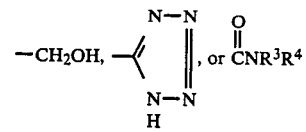

wherein $R^3$ and $R^4$ are the same or different and are H, lower alkyl, hydroxy, lower alkoxy or aryl, at least one of $R^3$ and $R^4$ being other than hydroxy and lower alkoxy; p is 1 to 4; Z is

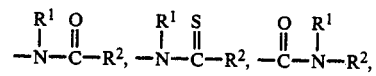

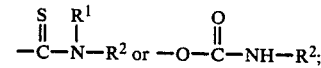

q is 1 to 12; $R^1$ is H or lower alkyl; and $R^3$ is H, lower alkyl, lower alkenyl, lower alkynyl, aryl, arylalkyl, lower alkoxy, aryloxy, arylalkyloxy, amino, alkylamino arylamino, arylalkylamino,

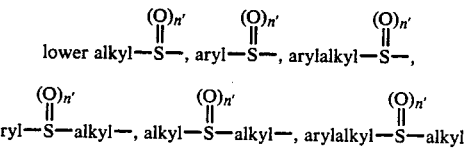

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

35 Claims, No Drawings

7-THIABICYCLOHEPTANE SUBSTITUTED DIAMIDE AND ITS CONGENER PROSTAGLANDIN ANALOGS

DESCRIPTION OF THE INVENTION

The present invention relates to 7-thiabicycloheptane substituted diamide and congener prostaglandin analogs which are cardiovascular agents useful, for example, in the treatment of thrombotic disease. These compounds have the structural formula

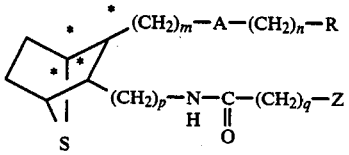

including all stereoisomers thereof, wherein m is 1 to 4; A is —CH=CH— or —CH$_2$—CH$_2$—; n is 1 to 5; R is CO$_2$H, CO$_2$alkyl, CO$_2$ alkali metal, CO$_2$polyhydroxyamine salt,

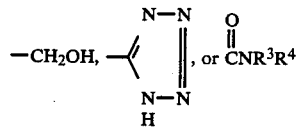

wherein R$^3$ and R$^4$ are the same or different and are H, lower alkyl, hydroxy, lower alkoxy or aryl at least one of R$^3$ and R$^4$ being other than hydroxy and lower alkoxy; p is 1 to 4; q is 1 to 12; and Z is

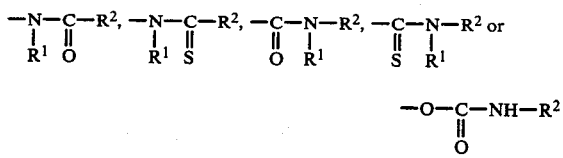

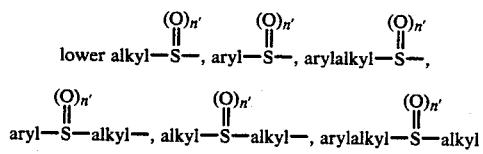

wherein R$^1$ is H or lower alkyl, and R$^2$ is lower alkyl, lower alkenyl, lower alkynyl, aryl, arylalkyl, lower alkoxy, arylalkyloxy, aryloxy, amino, alkylamino, arylalkylamino, arylamino,

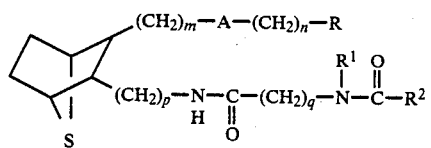

(wherein n' is 0, 1 or 2), alkylaminoalkyl, arylaminoalkyl, arylalkylaminoalkyl, alkoxyalkyl, aryloxyalkyl or arylalkoxyalkyl.

Thus, compounds of the invention within the scope of formula I include the following:

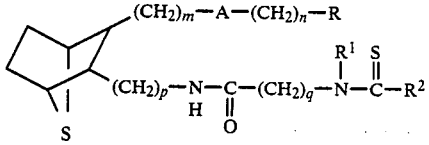

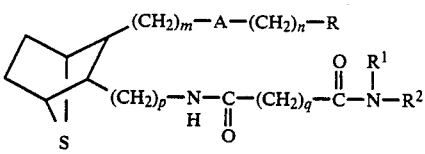

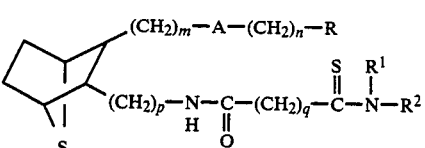

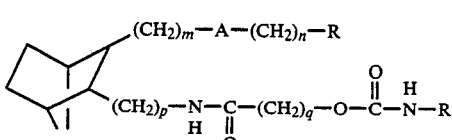

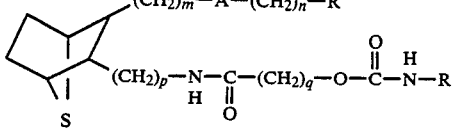

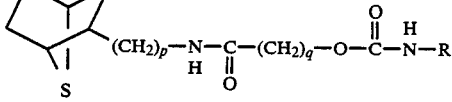

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms $(CH_2)_m$, $(CH_2)_n$ and $(CH_2)_p$ includes straight or branched chain radicals having from 1 to 4 carbons in the normal chain in the case of $(CH_2)_m$, from 1 to 5 carbons in the normal chain in the case of $(CH_2)_n$ and from 1 to 4 carbons in the normal chain in the case of $(CH_2)_p$ and may contain one or more lower alkyl and/or halogen substituents. Examples of $(CH_2)_m$, $(CH_2)_n$ and $(CH_2)_p$ groups include $CH_2$,

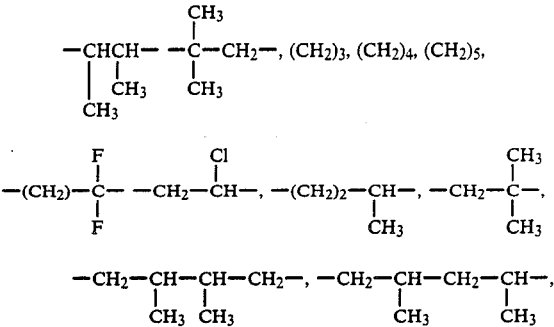

and the like.

The term $(CH_2)_q$ includes straight or branched chain radicals having from 1 to 12 carbons in the normal chain and includes any of the above examples of $(CH_2)_m$, $(CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

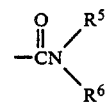

wherein $R^5$ and $R^6$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1 or 2, A is a —CH=CH—, n is 1 or 4, R is $CO_2H$ or $CH_2OH$; p is 1, $R^1$ is H, $(CH_2)_q$ is —$CH_2$—; Z is

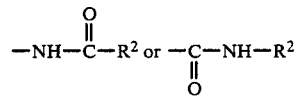

and $R^2$ is lower alkyl, such as pentyl, hexyl, or heptyl or lower alkoxy, such as pentoxy, lower alkylamino such as pentylamino or arylthioalkyl, such as phenylthiomethyl.

The compounds of formula I of the invention may be prepared as described below.

A. p is 1 and m is 1

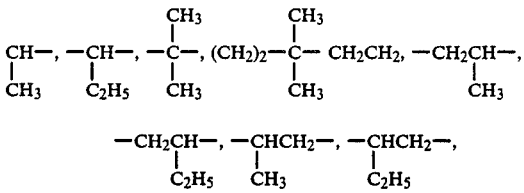  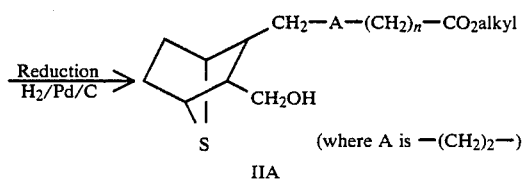

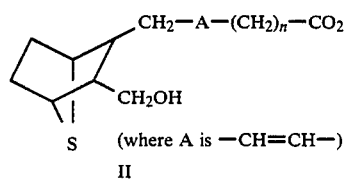

-continued
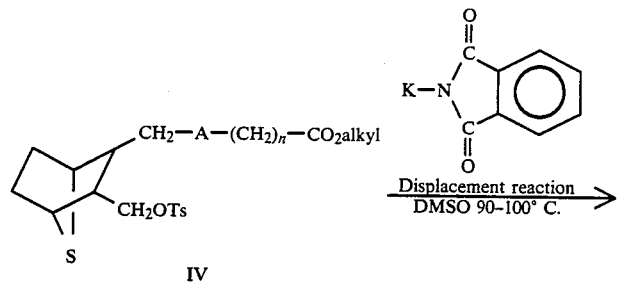
IV
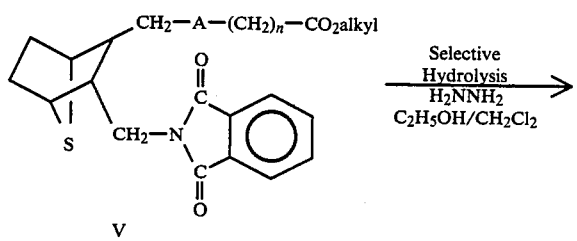
V
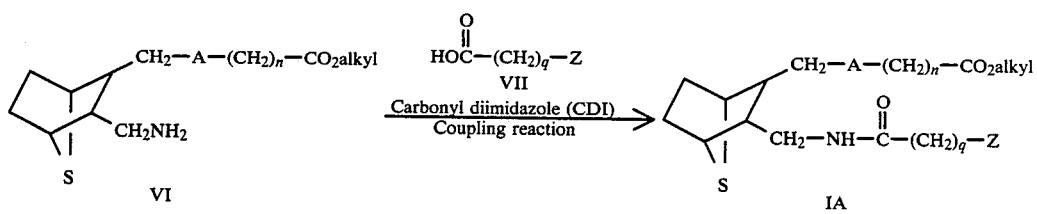
VI  VII  IA
B. Where p is 2 to 5 and m is 1
II or IIA $\xrightarrow{\text{Collins oxidation}}$
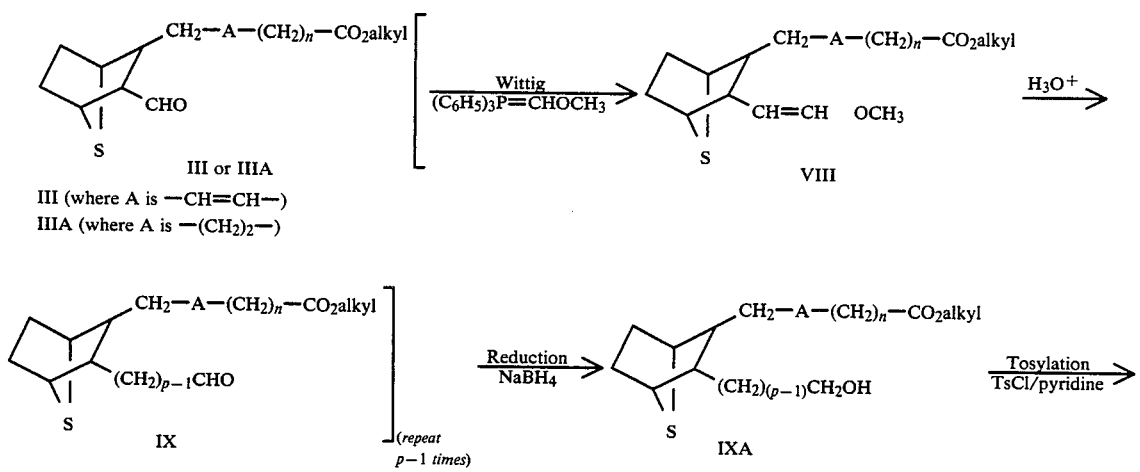
III or IIIA
III (where A is —CH=CH—)
IIIA (where A is —(CH$_2$)$_2$—)
VIII
IX   IXA
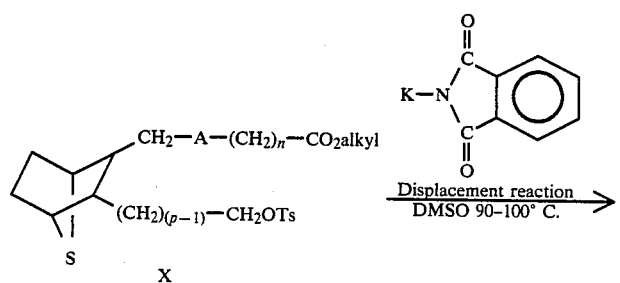
X

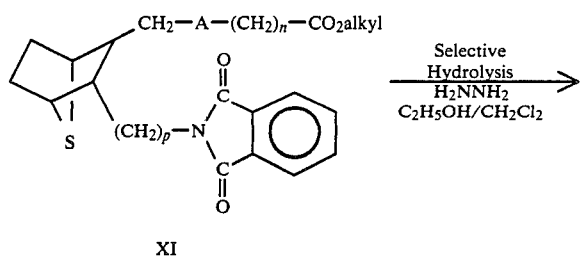
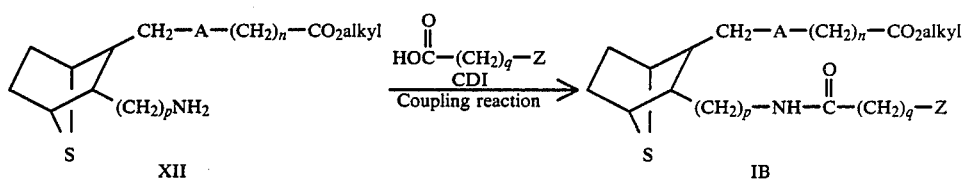
C. Where m is 2, p is 1 and A is —CH=CH—
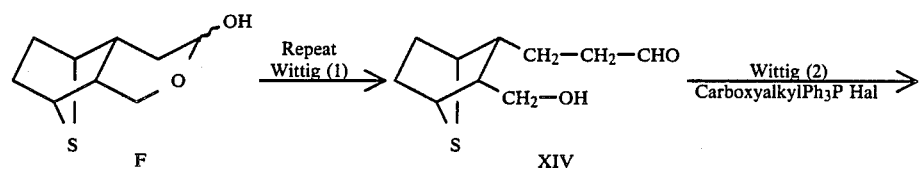
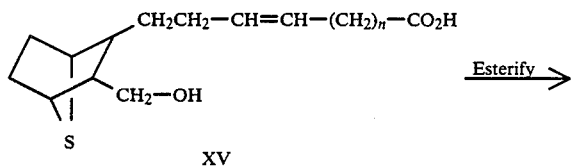
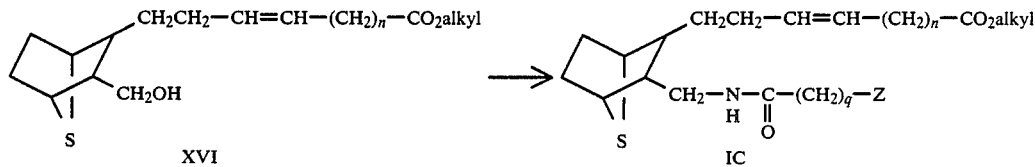
D. m is 2, p is 1 and A is —CH₂—CH₂
XVI $\xrightarrow{\text{Reduction}}{\text{H}_2/\text{Pd/C}}$
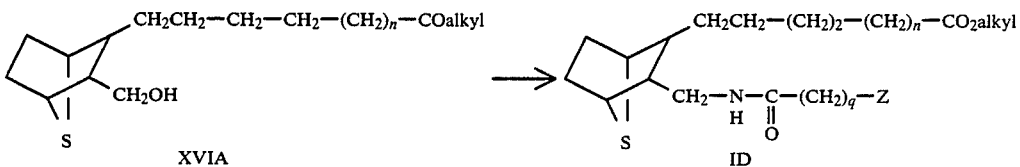
E. Where m is 3 or 4, p is 1 and A —CH=CH—
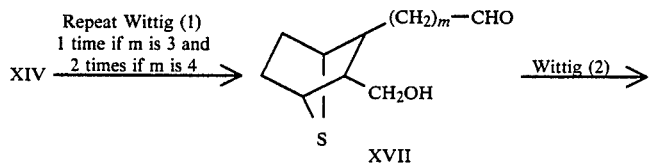

-continued

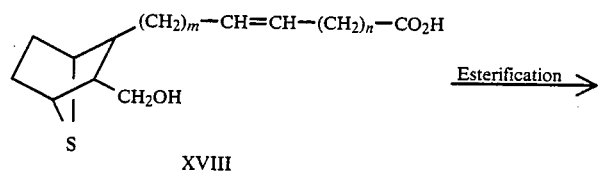
XVIII

Esterification →

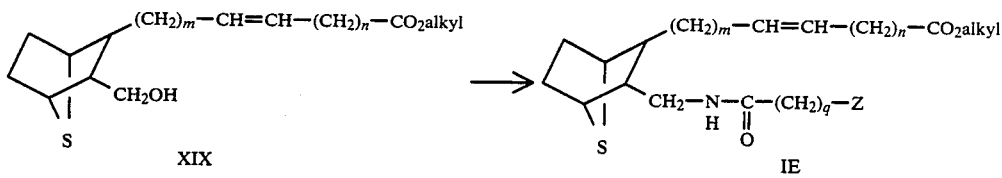
XIX          IE

F. Where m is 3 or 4, p is 1 and A is CH₂CH₂

XIX $\xrightarrow{\text{Reduction}}{\text{H}_2/\text{Pd/C}}$

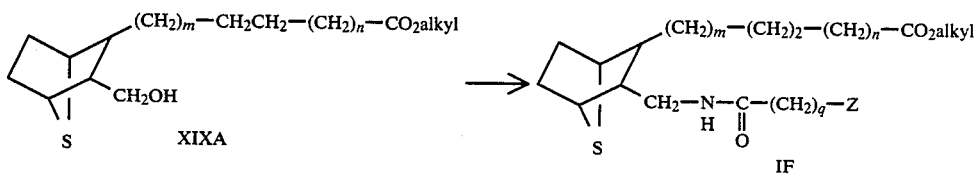
XIXA          IF

G. Where R is $\overset{\text{O}}{\underset{}{\text{C}}}$NR³R⁴ (wherein R³ and R⁴ are other than hydroxy or alkoxy)

IA, IB, IC, ID, IE, IF $\xrightarrow{\text{HNR}^3\text{R}^4}$

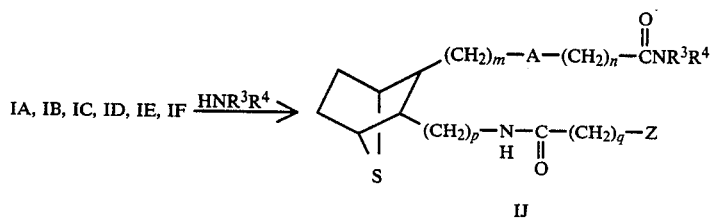
IJ

H. Where R is $-\!\!\!\underset{\underset{\text{H}}{\text{N}-\text{N}}}{\overset{\text{N}=\text{N}}{\|}}$ and A is CH=CH

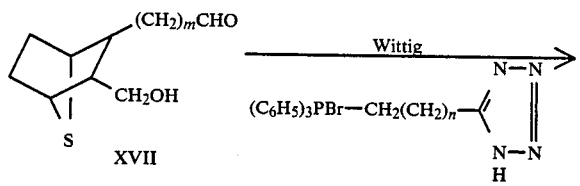
XVII $\xrightarrow{\text{Wittig}}$
$(C_6H_5)_3PBr-CH_2(CH_2)_n-\!\!\!\underset{\underset{\text{H}}{\text{N}-\text{N}}}{\overset{\text{N}=\text{N}}{\|}}$

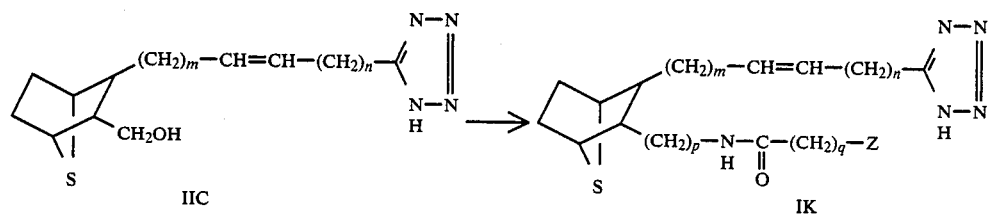
IIC          IK

K. Where R is $-\!\!\!\underset{\underset{\text{H}}{\text{N}-\text{N}}}{\overset{\text{N}=\text{N}}{\|}}$ and A is (CH₂)₂

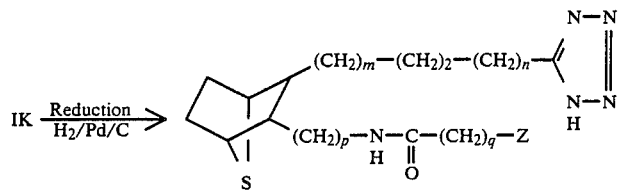
I. Where R is CH$_2$OH
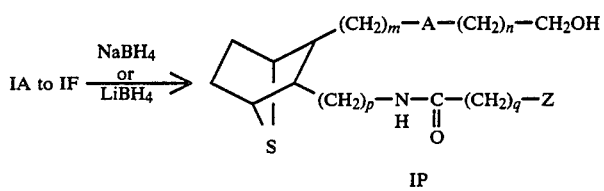
J. Where R is CO$_2$H
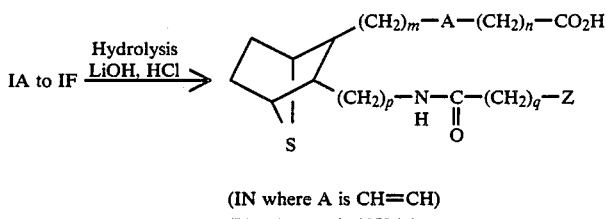
(IN where A is CH=CH)
(IO where A is (CH$_2$)$_2$)
K. Where R is $\overset{\overset{O}{\|}}{\underset{R^3}{C}}$N—OR$^{4'}$
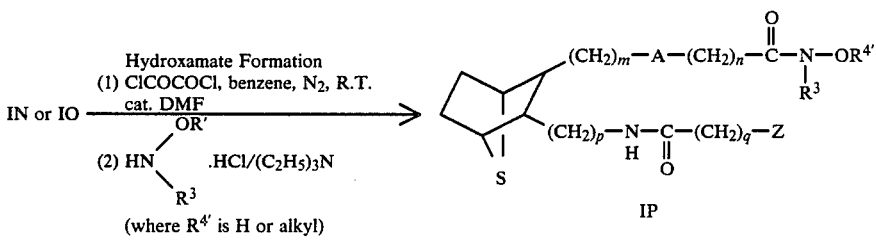
L. Where Z is —NH—$\overset{O}{\overset{\|}{C}}$—R$^2$, —NH—$\overset{S}{\overset{\|}{C}}$—R$^2$ or —O—$\overset{O}{\overset{\|}{C}}$—NH$_2$ and R$^2$ is NH$_2$
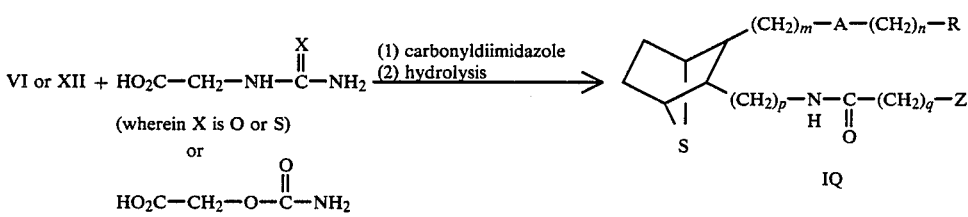
M. Preparation of starting material II
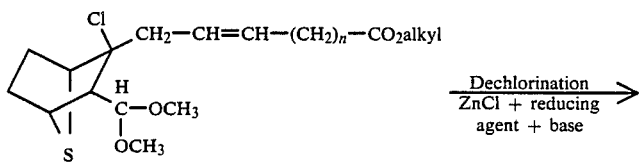

-continued

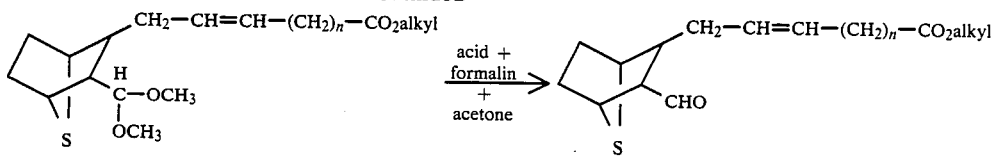

XXI acid +
formalin
+
acetone
→

XXII

↓ reducing agent

II

N. Preparation of starting material F

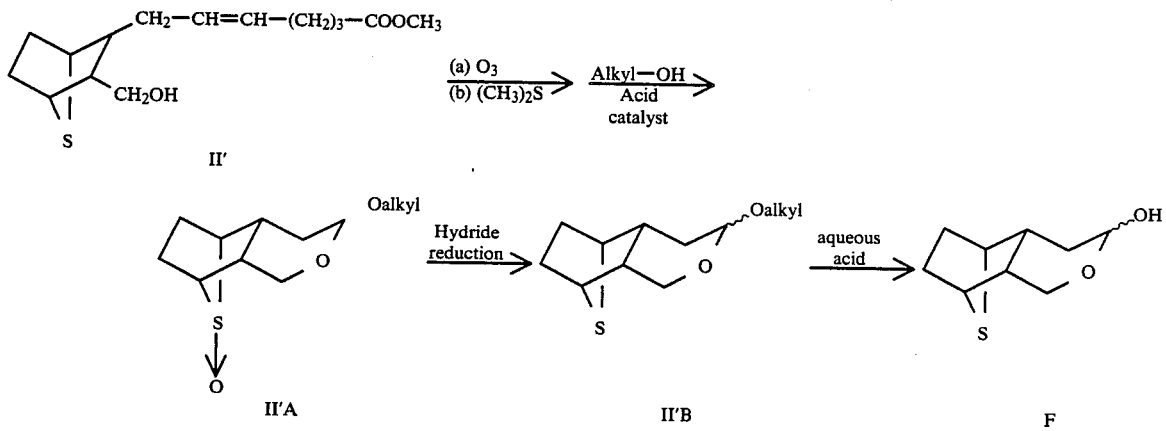

II′

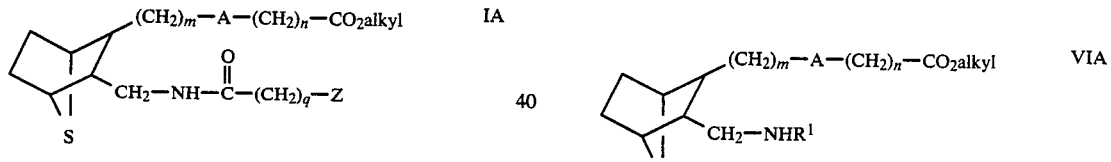

II′A    II′B    F

As seen in reaction sequence "A", compounds of the invention where p is 1 and R is CO₂ alkyl, that is

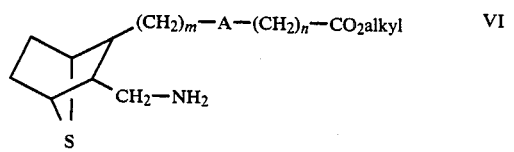 IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

VI

As seen in reaction sequence "A′", where $R^1$ is lower alkyl, an alkylation reaction is carried out as in the reference M. J. O'Donnell et al., *Tetrahedron Lett.* (1984), 25, 3651-33654 to give VIA

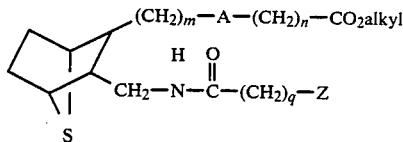 VIA

The amine VI is then subjected to a CDI coupling reaction by reacting VI with acid VII $$HO-\overset{O}{\underset{\|}{C}}-(CH_2)_q-Z$$  VII in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA

IA

The reaction sequence identified as "B" is employed to prepare compounds of the invention wherein p is 2 to 5, and R is CO₂alkyl, that is,

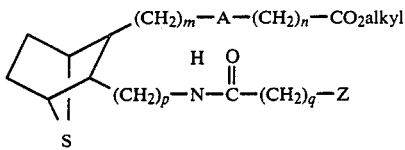

IB (where p is 2 to 5)

Compound II or IIA is used to form the aldehyde III (where A is —CH═CH—) or IIIA (where A is —(CH$_2$)$_2$). Thus, to form aldehyde III where A is —CH═CH—, comound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare aldehyde IX (where p is 2-5) by carrying out a homologation sequence, such as a Wittig reaction with (C$_6$H$_5$)$_3$P═CHOMe followed by hydrolysis, (p−1) times. The aldehyde IX (where p is 2-5) is then carried on to compounds of this invention where p is 2-5 by reducing aldehyde IX by reacting IX with a reducing agent such as sodium borohydride to form alcohol IXA

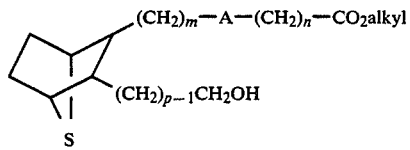

IXA tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

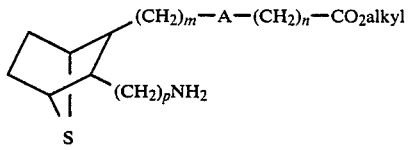

XII

The amine XII then reacted with acid VII in a CDI coupling reaction as described above to form the amide ester compound of the invention IB.

Compounds of the invention wherein m is 2, A is —CH═CH— and p is 1 may be prepared as outlined in reaction sequence "C" by subjecting starting compound F to a Wittig reaction, referred to as Wittig (1), by reacting F

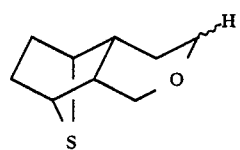

F (prepared as described hereinafter) with an alkoxymethyltriphenyl phosphonium halide, such as (methoxymethyl)triphenylphosphonium chloride, for example, as described in Example 4 of U.S. Pat. No. 4,143,054, to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —CH$_2$—CH$_2$—, and p is 1 may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH═CH— and p is 1 may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is CH$_2$CH$_2$, and p is 1 may be prepared by reducing hydroxymethyl compound XIX to form compound XIXA which is then employed in place of compound II in reaction scheme "A" to form compound IF of the invention.

Thus, compounds of the invention wherein m is 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

In reaction sequence "G", amides of the invention of structure IJ

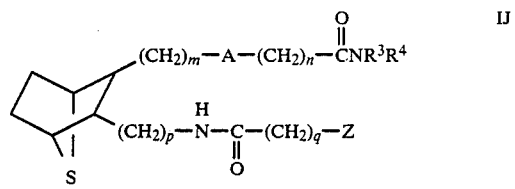

IJ wherein R$^3$ and R$^4$ are independently H, alkyl or aryl are prepared by treating ester IA to IF with an amine of the structure

HNR$^3$R$^4$. E

Compounds of the invention wherein R is tetrazole

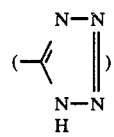

and A is CH═CH are prepared as described in reaction sequence "H" wherein alcohol XVII

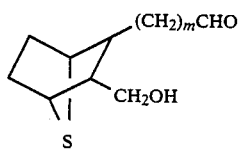

(prepared as described hereinafter) is reacted with a Wittig reagent of the structure G

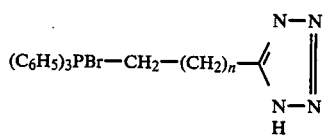

in the presence of a base, such as potassium t-butoxide or sodium hydride-dimethyl sulfoxide employing a molar ratio of XVII:G of within the range of from about 1:1 to about 0.2:1 to form the hydroxymethyl compound IIC

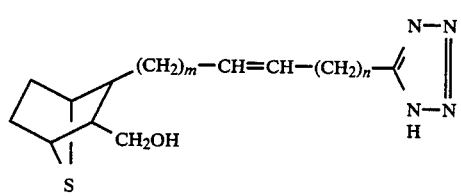

which may then be employed in reaction sequences "A" and "B" in place of compounds II or IIA to form compounds of the invention IK where A is —CH=CH— or IL where A is $(CH_2)_2$

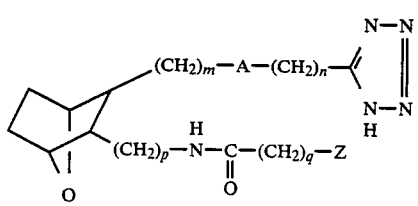

Alternatively, compound IL may be prepared by reducing compound IK by treating with $H_2$ in the presence of palladium on charcoal.

As seen in reaction sequence "I", compounds of the invention wherein R is $CH_2OH$ may be prepared by reducing esters IA to IF, by treatment with sodium borohydride or lithium borohydride to form compounds of the invention IM

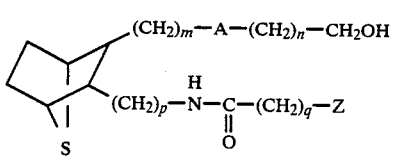

Referring to reaction sequence "J", the esters IA to IF can be converted to the free acid, that is, to

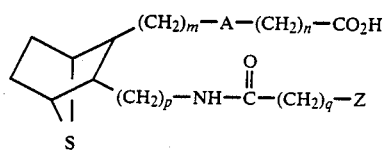

IN (A is —CH=CH—)
IO (A is $(CH_2)_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IN and IO.

In the reaction sequence identified as "K" where in Formula I, R is $$\begin{matrix} O & OR^{4'} \\ \parallel & / \\ CN & \\ & \backslash R^3 \end{matrix},$$

wherein $R^{4'}$ is H or alkyl, a solution of acid dissolved in an inert organic solvent such as benzene is treated with oxalyl chloride and a catalytic amount of dimethylformamide (DMF) and the mixture is stirred at room temperature under nitrogen. The resulting acid chloride is dissolved in an inert organic solvent such as tetrahydrofuran and the so-formed solution is added dropwise into a cold solution of amine hydrochloride H $$\begin{matrix} & OR^{4'} \\ & / \\ HN & .HCL \\ & \backslash R^3 \end{matrix} \quad H$$

(wherein $R^{4'}$ is H or alkyl, employing a molar ratio of acid chloride:H of within the range of from about 0.3:1 to about 1:1 and preferably from about 0.5:1) and triethylamine in aqueous tetrahydrofuran to form the hydroxamate IP.

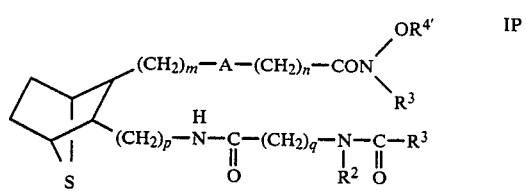

In reaction sequence "L" compounds of the invention wherein Z is $$-NH-\underset{\underset{O}{\parallel}}{C}-R^2, \quad -NH-\underset{\underset{S}{\parallel}}{C}-R^2 \text{ or } -O-\underset{\underset{O}{\parallel}}{C}-NH_2$$

and $R^2$ is $NH_2$, may be prepared by reacting amine VI or XII with an acid of the structure

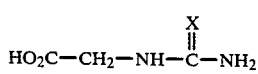

(wherein X is O or S) or

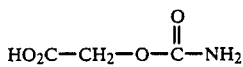 K in the presence of carbonyldiimidazole and then hydrolyzing the resulting product to form IQ.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

To form the sulfinyl and/or sulfonyl analogs of compounds of formula I wherein $R^3$ is —S—alkyl, —S—aryl, —S—alkylaryl, —alkyl—S—aryl, alkyl—S—alkyl, or —alkyl—S—alkylaryl, such formula I compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures.

The starting acid VII

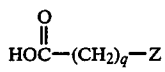 VII (wherein X is

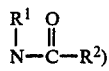)

may be prepared by reacting the amino acid L

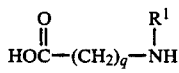 L or its acid chloride with acid chloride M

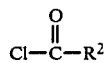 M (or its acid if the acid chloride of L is employed) in the presence of a strong base such as NaOH and water.

The starting alcohol II may be prepared as outlined in reaction sequence "M" starting with the chloride II

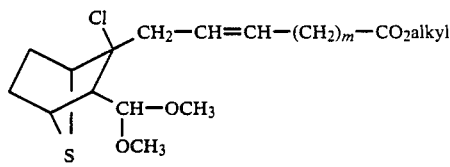 XX which is subjected to dechlorination by reaction with a mixture of zinc chloride and a reducing agent, such as sodium cyanoborohydride in the presence of an organic base such as triethylamine or pyridine, or sodium borohydride to form the acetal XXI

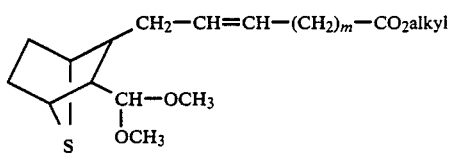 XXI

The acetal XXI is then converted to aldehyde XXII

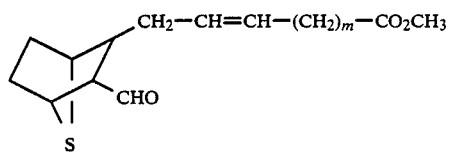 XXII by treating XXI with trifluoroacetic acid or other acid such as p-toluenesulfonic acid, hydrochloric acid or methanesulfonic acid, in the presence of formalin and acetone. Aldehyde XXII is then treated with reducing agent such as sodium borohydride in the presence of a solvent such as methanol at reduced temperatures to form alcohol II.

The starting chloride compound XX may be prepared according to the following reaction sequences.

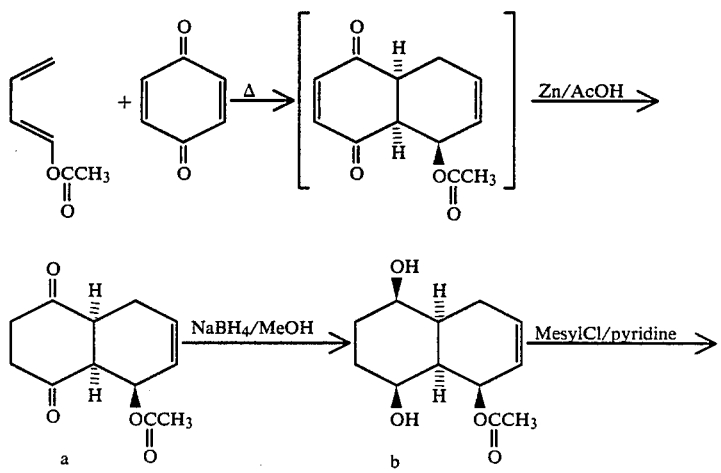

-continued
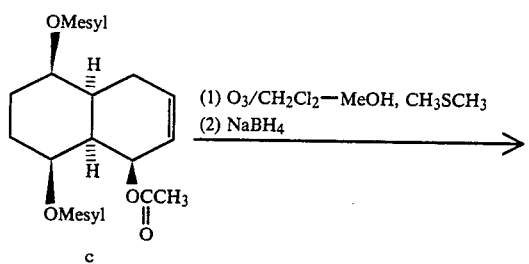
(1) O₃/CH₂Cl₂—MeOH, CH₃SCH₃
(2) NaBH₄
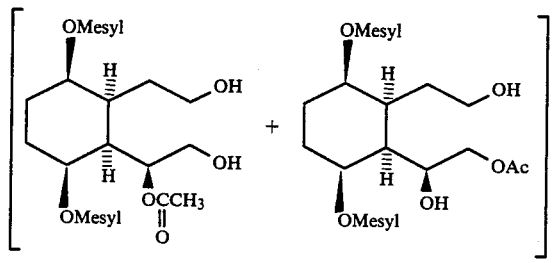
LiOH/THF—H₂O
MgSO₄
Amberlyst-15
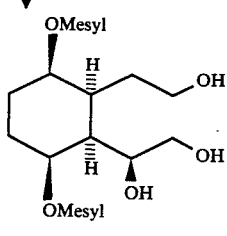
f
$$CH_3\underset{\underset{O}{\|}}{C}CH_3/\text{p-TsOH}$$
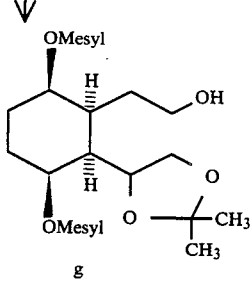
g
$$DMSO/ClC\underset{\underset{O}{\|}}{\overset{\overset{O}{\|}}{C}}Cl, Et_3N$$
CH₂Cl₂
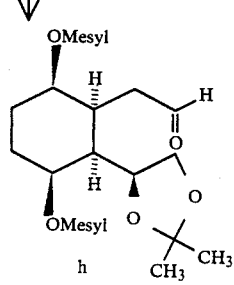
h -continued
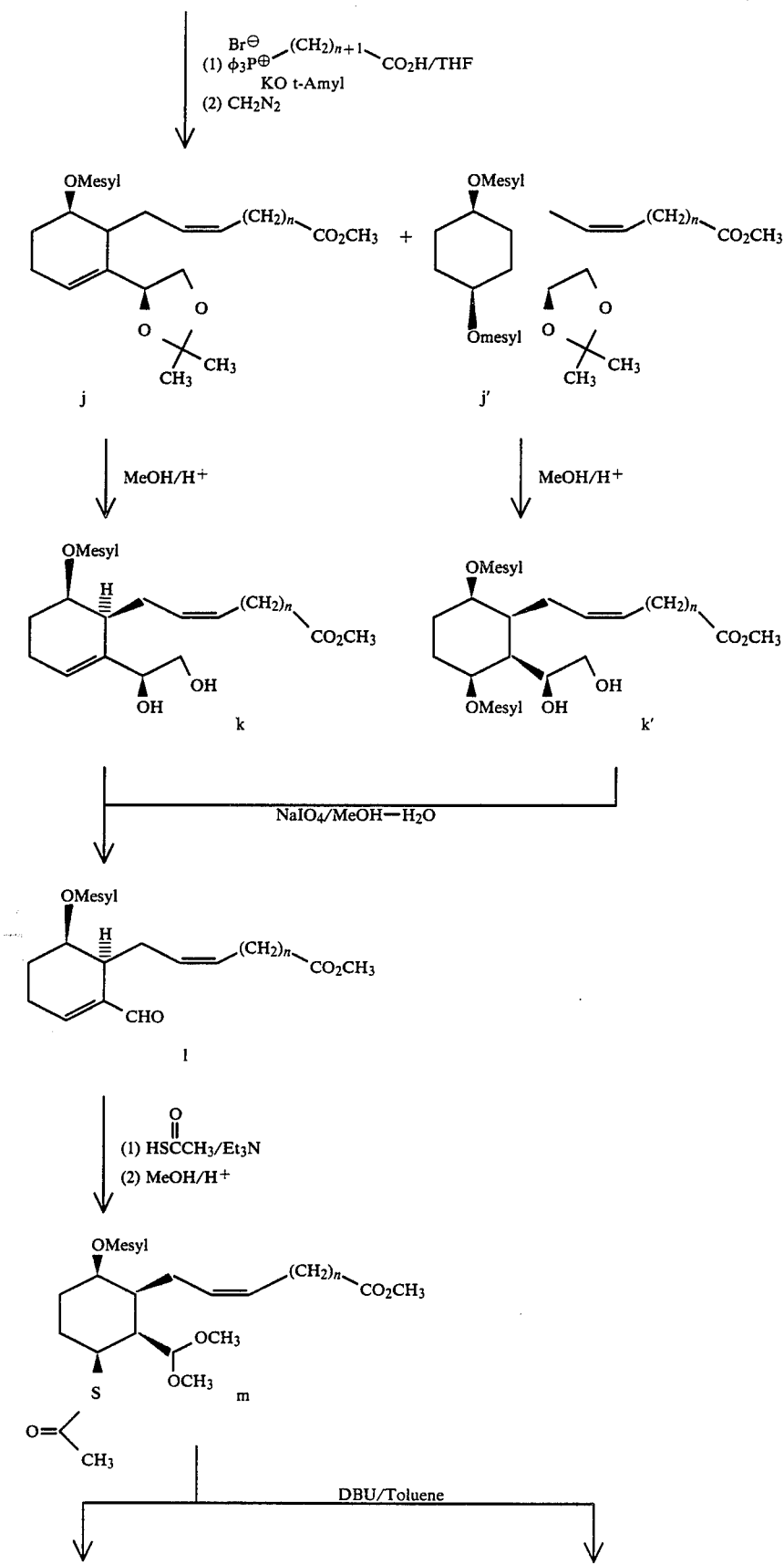

-continued

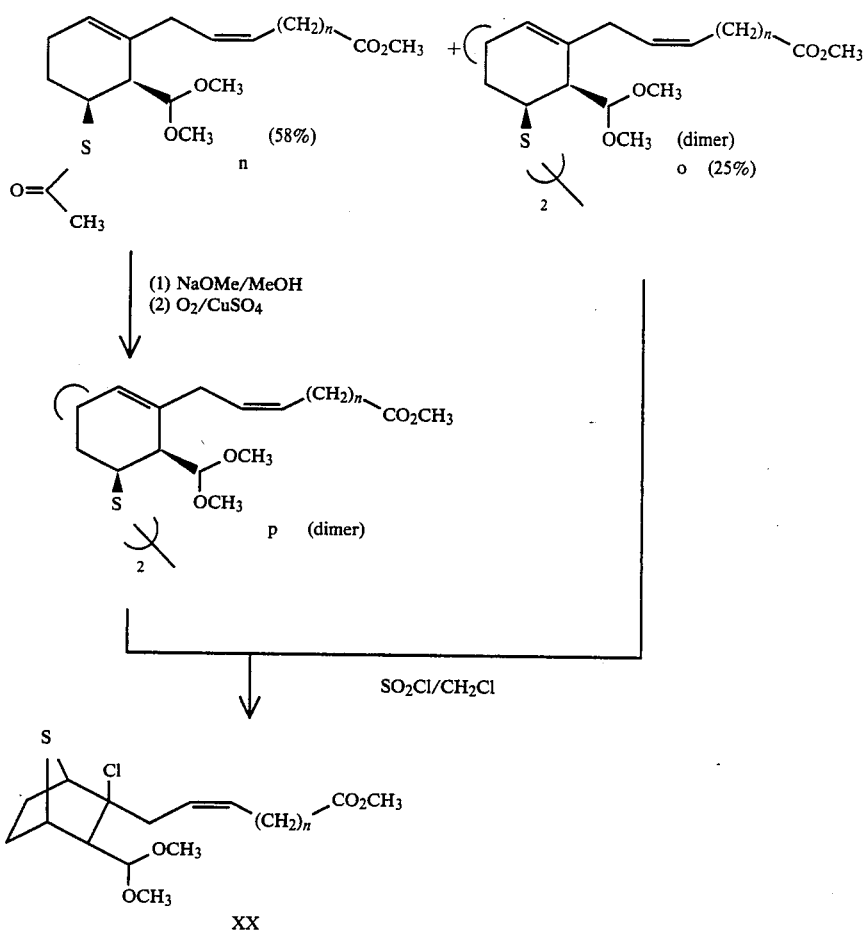

The starting material F

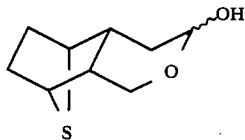   F may be prepared as outlined in reaction sequence "N" as follows.

A solution of alcohol II in acetone, methanol or methylene chloride is treated at reduced temperatures, for example, −78° C. to −60° C., with excess ozone, followed by cleavage of the intermediate ozonide with a dialkyl sulfide, for example, dimethylsulfide to provide after treatment with an alcohol (alkyl—OH) with an acid catalyst, i.e., p-toluenesulfonic acid, sulfoxide compound II′A

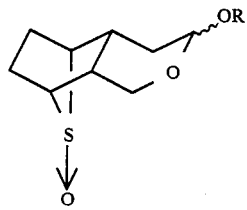  II′A

Treatment of sulfoxide II′A with a reducing agent, for example, lithium aluminum hydride provides sulfide II′B

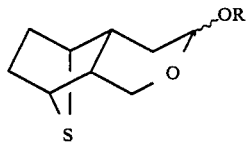  II′B which on aqueous hydrolysis under acid catalysis, for example, trifluoroacetic acid, provides hemi-acetal F

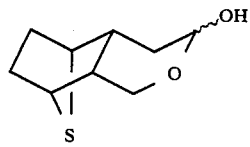  F

The starting acid VII wherein Z is

that is,

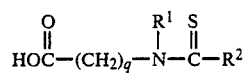 VIIA may be prepared by reacting the amino acid ester N

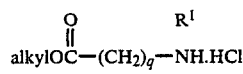 N with acid chloride O

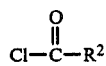 O in the presence of a base such as sodium carbonate and ether and water to form P

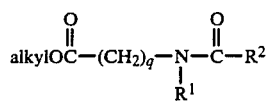 P and reacting P with phosphorus pentasulfide or Lawesson's reagent to form Q

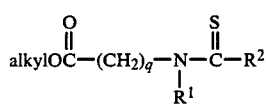 Q which is treated with strong base and water to form acid VIIA.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting acid VII wherein Z is

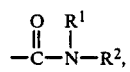

that is,

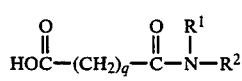 VIIIB wherein q is 2 may be prepared by reacting the amine R

HNR$^1$R$^2$    R with succinic anhydride

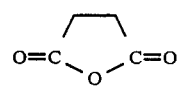

in the presence of ether to form acid VIIB

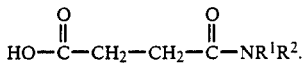 VIIB

Starting acid VIIB wherein q is 1 to 12 may be prepared by reacting amine R with ester S

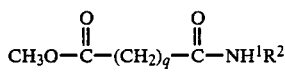 S in the presence of ethyl ether to form ester S'

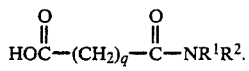 S' which may be hydrolyzed to the corresponding acid VIIB

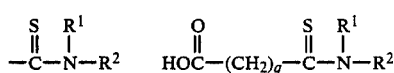 VIIB

The starting acid VII wherein Z is

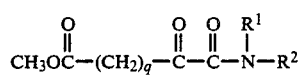 VIIC may be prepared by reacting the amino acid ester S'

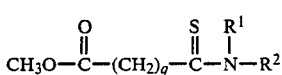 S' with phosphorus (IV) pentasulfide to form the ester S''

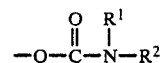 S'' which is then treated with a strong base such as NaOH and water to form VIIC.

The starting acid VII wherein Z is

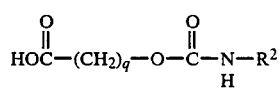

that is

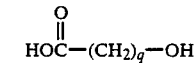 VIID may be prepared by reacting the ester-alcohol T

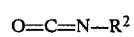 T with isocyanate U

O=C=N—R$^2$    U in the presence of an organic base such as triethylamine to form V

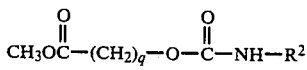

Compound V is treated with strong base such as sodium hydroxide and water to form VIID.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

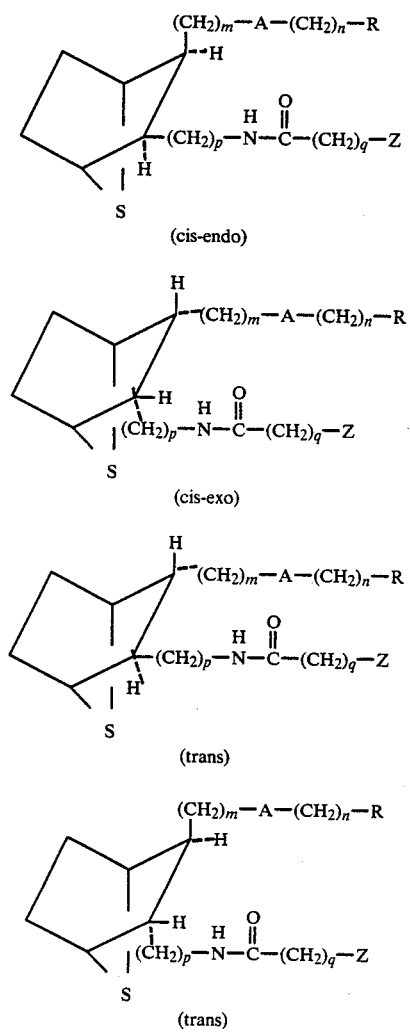

The nucleus in each of the compounds of the invention is depicted as

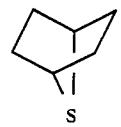

for matter of convenience; it will also be appreciated that the nucleus in the compounds of the invention may be depicted as

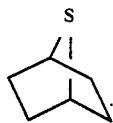

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following examples represent preferred embodiments of the present invention. Unless otherwise indicated, all temperatures are expressed in degrees Centigrade.

EXAMPLE 1

[1β,2α(5Z),3α,4β]-7-[3-[[[[(1-Oxohexyl)amino]acetyl]amino]methyl]-7-thiabicyclo[2.2.1]hept-2-yl]-5-heptenoic acid, methyl ester

A.
(4aα,5β,8aα)-5-(Acetyloxy)-1,2,3,4,-4a,5,8,8a-octahydro-1,4-naphthalenedione 1-Acetoxy-1,3-butadiene (150 g, 1.338 mole) was added to p-quinone (131 g, 1.213 mole) in CCl$_4$ (100 ml) and diisopropyl ether (350 ml). The reaction was heated in a steam bath with occasional swirling, until the reaction became homogeneous. The reaction was allowed to cool to 35° C. The reaction was then heated at reflux for one hour and concentraed in vacuo. Zn dust (200 g) was added portionwise to a mechanically stirred solution of the resulting straw-colored oil in Et$_2$O (100 ml) and glacial AcOH (500 ml) at 5°~10° C. The reaction was kept below 20° C. Stirring was continued for one hour at 5°~15° C. EtOAc (500 ml) was added to the reaction, which was filtered. The filter cake was washed with EtOAc (~800 ml). The filtrate was concentrated below 30° C. in vacuo to remove most of the acetic acid. The residue was dissolved in EtOAc (600 ml) and combined with the wash, which was washed with saturated NaHCO$_3$ (100 ml) and brine (200 ml×2). NaHCO$_3$ and brine washes were combined and re-extracted with EtOAc (400 ml). The EtOAc re-extract was washed with brine (100 ml×2). All the EtOAc layers were combined and dried over MgSO$_4$. Filtration and evaporation of solvent gave a straw-colored sludge. Diisopropyl ether (120 ml) was added and filtered. The resulting white powdery solids were washed again with diisopropyl ether (100 ml). The white solids (192 g) obtained were recrystallized from isopropyl alcohol (384 ml) to afford colorless crystals (178 g). The mother liquor and the diisopropyl ether washes were combined and crystallized in the same way to give additional crystals (30 g). Thus, the desired title compound (208 g, 0.937 mole, 77% from p-quinone) was obtained.

Cf J.O.C. (1964) 1341-1348, I. A. Kaye and R. S. Matthews.

B.

(1α,4α,4aβ,5α,8aβ)-1,2,3,4,4a,5,8,8a-Octahydro-1,4,5-naphthalenetriol, 5-acetate Part A compound (146 g, 0.657 mole) was dissolved in MeOH (1000 ml) and CH$_2$Cl$_2$ (500 ml). The reaction was cooled to −30° C.~−35° C. NaBH$_4$ (18.3 g, 0.495 mole) was added in portions under mechanical stirring. Stirring was continued for 2 hours at −30° C.~−35° C. after completion of the addition. The reaction was gradually warmed to −15° C. Then, NH$_4$Cl solution (NH$_4$Cl, 35 g in H$_2$O, 150 ml) was added. The reaction was vigorously stirred for 30 minutes at −15° C., and concentrated in vacuo to ~400 ml. Brine (100 ml) and saturated NH$_4$Cl (50 ml) were added to the residue. The products were extracted with EtOAc (1500 ml, 300 ml×2). The combined EtOAc layers were washed with brine (150 ml) and dried over Na$_2$SO$_4$. Filtration and evaporation of solvents gave a pale yellow oil (161 g), which was redissolved in MeOH (~300 ml) and concentrated to remove a possible impurity of boric acid. The resulting pale yellow oil (158 g) upon heating in diisopropyl ether (800 ml) under vigorous agitation, solidified. The solids were harvested, washed with diisopropyl ether (100 ml) to give white solids (116 g). The mother liquor and the wash were combined, and concentrated in vacuo to ~400 ml. Colorless crystals (8.9 g) were obtained from the concentrate. Thus, the desired title diol compound (124.9, 0.553 mole, 84%) was obtained.

Cf J.O.C. (1964) 1341-1348. I. A. Kaye and R. S. Matthews.

C.

(1α,4α,4aβ,5α,8aβ)-1,2,3,4,4a,5,8,8a-Octahydro-1,4,5-naphthalenetriol, 5-acetyl-1,4-bis(methanesulfonate)

Part B diol (50 g, 0.221 mole) was suspended in pyridine (250 ml) and cooled to 0° C. Mesyl chloride (50 ml, 0.646 mole) was added dropwise. Stirring was continued at 0° C. for one hour. The reaction was gradually warmed to room temperature and left overnight. The reaction was poured into ice (~500 ml) and stirred for one hour. The resulting white precipitate was harvested and washed with water until the wash became neutral (~pH 5). The white solids were dried in a heated vacuum oven at 40° C.-50° C. The desired title dimesylate product (75 g, 0.196 mole, 88%) was obtained.

Cf J.O.C. (1964) 1341-1348, I. A. Kaye and R. S. Matthews.

D, E, and F.

(1α,2β,3β,4α)-2-[(S*)-1,2-Dihydroxyethyl]-3-(2-hydroxyethyl)-1,4-cyclohexanediol, 1,4-bis(methanesulfonate)(F)

Part C dimesylate (72 g, 0.188 mole) was dissolved in CH$_2$Cl$_2$ (540 ml) and MeOH (208 ml). After the solution was cooled to −78° C., O$_3$ was introduced until the reaction became blue. An excess of O$_3$ was purged with a stream of O$_2$ for 20 minutes, followed by N$_2$ for 30 minutes. Dimethyl sulfide (29.2 ml) was added and the reaction was warmed to −30° C. gradually. Additional MeOH (400 ml) was added and the reaction was stirred for 30 minutes at −30° C. Then NaBH$_4$ (14.8 g, 0.4 mole) was added portionwise over 20 minutes. The reaction was gradually warmed to −10° C. and stirred for one hour. NH$_4$Cl (53 g) in H$_2$O (150 ml) was added and the reaction was concentrated in vacuo to ~300 ml. Brine (100 ml) was added to the residue, which was extracted with EtOAC (800 ml, 400 ml×3). The combined EtOAc layers were dried over MgSO$_4$. Filtration and evaporation of solvents gave a colorless heavy oil (95 g). MeOH (300 ml) was added to the oil and the resulting homogeneous solution was concentrated to dryness to remove a possible impurity of boric acid. A pale yellow oil (81 g, a mixture of secondary acetate (D) and primary acetate (E)) was obtained. LiOH.H$_2$O (15.8 g) dissolved in H$_2$O (100 ml) was added to the oil (81 g) dissolved in THF (1300 ml). The reaction was mechanically stirred for 4 hours at room temperature. MgSO$_4$ (solid, 75 g) was added and the reaction was filtered. The filter cake was washed with THF (300 ml). The filtrate and the washes were combined and treated with Amberlyst-15 resin (35 g). The reaction was stirred for 5 minutes and filtered through Celite, which was washed with THF (200 ml). The filtrate and the washes were combined and concentrated in vacuo to give a viscous oil (61.5 g), which partially solidified upon standing in a cold room. The resulting solid title triol was crystallized from isopropanol (210 ml) to give white solids (59.68 g, 0.159 mole, 84% from Part C dimesylate).

Anal Calcd for C$_{12}$H$_{2}$O$_{9}$S$_2$: C, 38.28; H, 6.42; S, 17.03. Found: C, 38.31, H, 6.46; S, 16.97.

G.

(1α,2β,3β,4α)-2-[(S*)-2,2-Dimethyl-1,3-dioxolan-4-yl]-3-(2-hydroxyethyl)-1,4-cyclohexanediol, 1,4-bis(methanesulfonate)

p-TosylOH.H$_2$O (260 mg, 0.00126 mole) was added to a magnetically stirred suspension of Part F triol (61 g, 0.162 mole) in acetone (1600 ml, dried over $B_2O_3$). The reaction became homogeneous in 30 minutes and stirring was continued overnight. 3A molecular sieve (30 g) was added and the reaction was stirred for an additional 2.5 hours. Then, $NaHCO_3$ (1.1 g, 0.0131 mole) in $H_2O$ (15 ml) was added. The reaction was filtered through a Celite pad, and concentrated in vacuo to give white solids (69 g). Slow addition of diisopropyl ether to the solids dissolved in hot acetone (100 ml) gave the title alcohol in the form of a white fine powder (65.5 g, 0.157 mole, 97%).

Anal Calcd for $C_{15}H_{28}O_9S_2$: C, 43.25; H, 6.77; S, 15.39. Found: C, 43.35; H, 6.84; S, 15.35.

H.

(1α,2α,3β,6β)-2-[(S*)-2,2-Dimethyl-1,3-dioxolan-4-yl]-3,6-bis[(methylsulfonyl)oxy]cyclohexaneacetaldehyde DMSO (5.08 ml) in $CH_2Cl_2$ (30 ml) was added dropwise to oxalyl chloride (2.296 ml) in $CH_2Cl_2$ (100 ml) at −78° C. The reaction was stirred at −78° C. for 15 minutes, followed by addition of Part G alcohol (10 g) in $CH_2Cl_2$ (100 ml) very slowly. Stirring was continued for 15 minutes at −78° C., then $Et_3N$ (17.5 ml) was added dropwise at −78° C. and the reaction was gradually warmed to room temperature. Water (100 ml) was added and the water layer separated was further extracted with $CH_2Cl_2$ (240 ml×2). The combined $CH_2Cl_2$ layers were washed with $H_2O$ (120 ml×3) and dried over $MgSO_4$. Filtration and evaporation of solvent gave a pale straw-colored oil, which was dried by azeotropic distillation with benzene several times. Title aldehyde in the form of a pale straw-colored foam (10.1 g) was obtained. This was used for the subsequent reaction without any purification.

J. (and J')

(Z)-7-[(cis)-2[(S*)-2,2-Dimethyl-1,3-dioxolan-4-yl]-6-[(methylsulfonyl)oxy]-2-cyclohexen-1-yl]-5-heptenoic acid, methyl ester (J)

To (4-carboxybutyl)triphenylphosphonium bromide (15.948 g, 36 mmole) suspended in THF (150 ml) was added KO t-amylate in toluene (1.6M, 45 ml) dropwise at room temperature. After stirring for 6 hours at room temperature, a burgundy colored solution was obtained. Part H aldehyde (crude product, 10.1 g, 24 mmole) dissolved in THF (20 ml) was cooled to −30° C.~−40° C. The ylid solution (190 ml) was added dropwise over 40 minutes. The reaction was stirred at −40° C. for one hour and at room temperature overnight. The reaction was quenched with saturated $NH_4Cl$ (40 ml) and brine (50 ml). The products were extracted with EtOAc (400 ml, 200 ml×3), which was dried over $MgSO_4$. Filtration and evaporation of solvents gave a straw-colored oil (15.3 g). This was suspended in $Et_2O$ and treated with $CH_2N_2$ until the desired acid was esterified. The solvent was evaporated off in vacuo and the residue was purified by $SiO_2$ column (silica 60, 300 g) eluted with $Et_2O$/petroleum ether=1/1 and $Et_2O$ to give title compound (4.8 g, 11.52 mmole, 48%). Depending upon the amount of the ylid used, compound (Z)-7-[(1α,2α,3α,6α)-2-[(S*)-2,2-dimethyl-1,3-dioxolan-4-yl]-3,6-bis[(methylsulfonyl)oxy]cyclohexy]-5-heptenoic acid, methyl ester (J') can be obtained.

K.

(Z)-7-[(cis)-2-[(S*)-1,2-Dihydroxyethyl]-6-[(methylsulfonyl)oxy]cyclohexyl]-5-heptenoic acid, methyl ester To Part J compound (5.59 g, 13.45 mmole) dissolved in MeOH (56 ml) was added p-TsOH.$H_2O$ (140 mg, 0.73 mmole), and the reaction was stirred at room temperature overnight. Saturated $NaHCO_3$ (10 ml) was added and MeOH was removed in vacuo. The residue was partitioned between EtOAc (100 ml) and brine (50 ml). The water layer was further extracted with EtOAc (100 ml×2). The combined EtOAc layers were washed with brine (50 ml) and dried over $MgSO_4$. Filtration and evaporation of solvent gave an oil (5.723 g), which was purified by $SiO_2$ column (silica 60, 150 g) eluted with 5% MeOH in $CH_2Cl_2$ to give the starting material (1.1 g, 2.6 mmole) and the desired title diol (3.3 g, 9.2 mmole, 85%).

L.

(Z)-7-[(cis)-2-Formyl-6-[(methylsulfonyl)oxy]-2-cyclohexen-1-yl]-5-heptenoic acid, methyl ester $NaIO_4$ (2.19 g, 10.1 mmole) suspended in $H_2O$ (4 ml) was added to Part K diol (3.5 g, 9.2 mmole) in MeOH (36 ml) at 0° C. Stirring was continued for 1.5 hours at room temperature. 10% $Na_2S_2O_3$ (10 ml) was added to the reaction. The reaction was stirred for 10 minutes, and poured into $Et_2O$ (100 ml) and $H_2O$ (20 ml). The products were extracted into the $Et_2O$ layer. The water layer was further extracted with $Et_2O$ (50 ml×3). The combined $Et_2O$ layers were washed with brine (50 ml) and dried over $MgSO_4$. Filtration and evaporation of solvents gave a pale yellow oil (3.1 g). The crude products were used for the subsequent reaction.

M.

(Z)-7-[(1α,2α,3α,6α)-3-(Acetylthio)-2-(dimethoxymethyl)-6-[(methylsulfonyl)-oxy]cyclohexyl]-5-heptenoic acid, methyl ester $CH_3COSH$ (9 ml, 0.102 mole) and $Et_3N$ (9 ml, 0.065 mole) were added to the crude Part L product (3.1 g, 9 mmole) in $CH_2Cl_2$ (230 ml) at −20° C. The reaction was stirred for four hours at −20° C.~−10° C. and one hour at −10°~0° C. The reaction was poured into saturated $NaHCO_3$ and the products were extracted into $CH_2Cl_2$. The water layer was further extracted with $CH_2Cl_2$ (100 ml×3). The combined $CH_2Cl_2$ layers were washed with saturated $NaHCO_3$ and brine and dried over $MgSO_4$. Filtration and evaporation of solvent gave a crude oil (4.1 g). The crude oil (4.1 g) was dissolved in MeOH [300 ml, dried over Mg(OMe)$_2$] and treated with p-TsOH.$H_2O$ (240 mg, 1.26 mmole) overnight at room temperature. $NaHCO_3$ (1.2 g) in $H_2O$ (5 ml) was added to the reaction and MeOH was mostly removed in vacuo. The residue (~10 ml) was poured into $Et_2O$ (150 ml) and $H_2O$ (30 ml). The products were extracted into the $Et_2O$ layer. The water layer was further extracted with $Et_2O$ (100 ml×2). The combined $Et_2O$ layers were washed with brine (50 ml) and dried over $MgSO_4$. Filtration and evaporation of solvent gave a pale yellow oil (4.2 g) which was purified by $SiO_2$ column (silica 60, 120 g) eluted with $Et_2O$/petroleum ether=1/1 and $Et_2O$/petroleum ether=2/1, to give desired title acetal (3.01 g, 6.4 mmole, 70% from Part H diol).

N.

(Z)-7-[(cis)-5-(Acetylthio)-6-(dimethoxymethyl)-1-cyclohexen-1-yl]-5-heptenoic acid, methyl ester To Part J mesylate (3.01 g, 6.43 mmole) dissolved in toluene (30 ml) was added 1,8-diazabicyclo[5.4.0]undec-7-ene (DBU) (5.5 g, 36 mmole). The reaction was warmed to 80° C. under magnetic stirring for 18 hours. The reaction was poured into Et$_2$O (130 ml) and washed with 0.5N-HCl (30 ml). The HCl wash was re-extracted with Et$_2$O (70 ml). The combined Et$_2$O layers were washed with 0.5N-HCl (30 ml), H$_2$O (30 ml×3) and dried over MgSO$_4$. Filtration and evaporation of the solvent gave a straw-colored oil (2.4 g), which was purified by SiO$_2$ column (silica 60, 80 g) eluted with Et$_2$O/petroleum ether=1/2 to give title thioacetate (1.41 g, 3.8 mmole, 58%) and disulfide described in Part O (0.58 g, 1.6 mmole, 25%) as colorless oils.

O.

5,5'-Bis[(Z)-7-[(cis)-6-(dimethoxymethyl)-1-cyclohexen-1-yl]-7-heptenoic acid, methyl ester]disulfide Solid NaOMe (84 mg, 1.6 mmole) was added to a magnetically stirred solution of Part N thioacetate (580 mg, 1.6 mmole) in MeOH (58 ml) at room temperature. Hydrolysis of thioacetate was completed in 2 hours at room temperature. O$_2$ was then bubbled through the reaction for 2 days. Saturated NH$_4$Cl (10 ml) and saturated CuSO$_4$ (100 μl) were added and O$_2$ was again bubbled through the reaction to complete disulfide formation. The reaction was concentrated in vacuo to remove most of MeOH. The products were extracted with Et$_2$O (100 ml, 50 ml). The combined Et$_2$O layers were washed with H$_2$O (30 ml×2) and dried over MgSO$_4$. Filtration and evaporation of the solvent gave a straw-colored oil (530 mg) which was purified by SiO$_2$ column (silica 60, 30 g) eluted with Et$_2$O/petroleum ether 1/4~1/2 to give the desired title disulfide (452 mg, 0.69 mmole, 85%) as a colorless oil.

Anal Calcd for C$_{34}$H$_{54}$O$_8$S$_2$: C, 62.35; H, 8.31; S, 9.79. Found: C, 62.28; H, 8.19; S, 9.77.

P.

[1β,2α(E),3α,4β]-7-[2-Chloro-3-(dimethoxymethyl)-7-thiabicyclo[2.2.1]-hept-2-yl]-5-heptenoic acid, methyl ester SO$_2$Cl$_2$ (63 μl, 0.784 mmole) in CH$_2$Cl$_2$ (5 ml) was added dropwise to a magnetically stirred solution of Part O disulfide (515 mg, 0.783 mmole) in CH$_2$Cl$_2$ (7.8 ml) at −78° C. over 30 minutes. Stirring was continued for 2 hours at −78° C. 10% Na$_2$S$_2$O$_3$ (10 ml) and saturated NaHCO$_3$ (10 ml) were added and the reaction was warmed to room temperature. The reaction was poured into CH$_2$Cl$_2$ (50 ml) and the products were extracted into the CH$_2$Cl$_2$ layer. The water layer was further extracted with CH$_2$Cl$_2$ (50 ml×2). The combined CH$_2$Cl$_2$ layers were washed with H$_2$O (30 ml×2) and dried over MgSO$_4$. Filtration and evaporation of solvent gave a colorless oil (568.5 mg, quantitative recovery).

Q.

[1β,2α(Z),3α,4β]-7-[3-(Dimethoxymethyl)-7-thiabicyclo[2.2.1]hept-2-yl]-5-heptenoic acid, methyl ester ZnCl$_2$ (313.2 mg, 2 mmole) and NaCNBH$_3$ (285 mg, 4 mmole) were dried under vacuum and heated (~50°-60° C.) for 20 minutes. Then Et$_2$O (20 ml) was added and the reaction was stirred for 30 minutes at room temperature, followed by an addition of Et$_3$N (320 μl, 2.3 mmole). After 30 minutes stirring at room temperature, Part P chloride (crude products, 568.5 mg) in Et$_2$O (10 ml) was added at room temperature. The reaction was stirred overnight at room temperature. Saturated NaHCO$_3$ (3 ml) was added and the reaction was poured into Et$_2$O (100 ml). The products were extracted into the Et$_2$O layer. The water layer was further extracted with Et$_2$O (100 ml). The combined Et$_2$O layers were washed with saturated NaHCO$_3$ (25 ml), H$_2$O (25 ml×2) and dried over MgSO$_4$. Filtration and evaporation of the solvent gave a colorless oil, which was purified by silica gel column (Baker silica gel for flash chromatography, 20 g) eluted with Et$_2$O/petroleum ether-1/4 to give the desired title product (379 mg, 1.155 mmole, 74% from part O disulfide.

Anal Calcd for C$_{17}$H$_{28}$O$_4$S: C, 62.16; H, 8.59; S, 9.76. Found: C, 62.13; H, 8.42; S, 9.76.

R.

[1α,2β(5Z),3β,4α]-7-[3-Formyl-7-oxabicyclo[2.2.1]hept-2-yl]-5-heptenoic acid, methyl ester Acetal (prepared as described in Part Q) (850 mg, 2.59 mmol) was dissolved in acetone (20 ml) and 37% formaldehyde solution (53 ml). The solution was cooled in an ice bath and distilled CF$_3$COOH (7.4 ml) was added. After stirring at 0°-5° C. for 8¾ hours, saturated NaHCO$_3$ solution was added until no more gas evolution was observed. The product was extracted into ether (3×150 ml), washed with water (3×75 ml), dried (MgSO$_4$), filtered and freed of solvent in vacuo. The remaining colorless oil was twice dissolved in benzene and taken to dryness in vacuo leaving a colorless oil (821 mg) which was a mixture of the desired aldehyde ([1α,2β(5Z),3β,4α]-7-[3-formyl-7-thiabicyclo[2.2.1]hept-2-yl]-5-heptenoic acid, methyl ester) and the starting acetal.

S.

[1α,2β(5Z),3β,4α]-7-[3-Hydroxymethyl-7-thiabicyclo[2.2.1]hept-2-yl]-5-heptenoic acid, methyl ester The oil mixture from Part R was dissolved in methanol (30 ml) and cooled to 0° C. NaBH$_4$ (98 mg, 2.59 mmol) was added portionwise. After stirring at 0° C. for 20 minutes, most of the MeOH was removed in vacuo. The residue was partitioned between Et$_2$O (100 ml) and 1N HCl solution (30 ml). The aqueous layer was reextracted with Et$_2$O (2×30 ml). The combined Et$_2$O extracts were washed with saturated NaCl solution (2×30 ml), dried (MgSO$_4$) and freed of solvent in vacuo leaving an oil. This was chromatographed on silica gel (Baker silica gel-for flash chromatography, 40 g) eluting with ether-pet ether 1:1. After eluting the acetal from Part Q (172 mg, 20%), the desired title alcohol ester was obtained (497.4 mg, 67.6% from acetal from Part Q).

Anal Calcd for C$_{15}$H$_{24}$O$_3$S: C, 63.35; H, 8.51; S, 11.27. Found: C, 63.48; H, 8.56; S, 11.07.

TLC: silica gel, Et$_2$O-pet ether 1:1, UV+vanillin, R$_f$=0.22.

T. N-Hexanoylglycine

Glycine (7.5 g, 100 mmol) was dissolved in NaOH solution (NaOH:8 g, H$_2$O:50 ml) and cooled to 0° C. Et$_2$O (50 ml) was added and n-hexanoyl chloride (13.4 g, 100 mmol) was then added dropwise over 60 minutes at 0° C. under vigorous stirring. The reaction was allowed to warm to room temperature and was stirred for 1 hour. 1N-NaOH (10 ml) was added and layers were separated. The water layer was washed with Et$_2$O (20 ml×2). The combined Et$_2$O layers were extracted with 1N-NaOH (20 ml). The combined water layers were acidified with concentrated HCl to pH 2 and the products were extracted with Et$_2$O (100 ml×3). The combined Et$_2$O layers were washed with brine (50 ml) and dried over MgSO$_4$. Filtration and evaporation of solvent gave a colorless solid (16.2 g), which was crystallized from EtOAc (60 ml) to give colorless needle crystals (10.9 g, 63 mmol, 63%), m.p. 93°–96°. TLC: silica gel, MeOH, CH$_2$Cl$_2$, HCOOH; 10, 89.5, 0.5, PMA R$_f$=0.45.

U.

[1β,2α(5Z),3α,4β]-7-[3-(Tosyloxymethyl)-7-thiabicyclo[2.2.1]hept-2-yl]-5-heptenoic acid, methyl ester Tosyl chloride (22.4 mmol) dissolved in CH$_2$Cl$_2$ (30 ml) is added dropwise to a magnetically stirred solution of Part S [1β,2α(5Z),3α,4β]]-7-[3-(hydroxymethyl)-7-thiabicyclo[2.2.1]hept-2-yl]-5-heptenoic acid, methyl ester (11.2 mmol) in pyridine (30 ml) at 0° C. After completion of the addition, the reaction is warmed to room temperature and stirred overnight. The reaction is poured into ice/H$_2$O and stirred for 30 minutes. The products are extracted with EtOAc (80 ml×3). The combined EtOAc layers are washed with 3N-HCl (40 ml×3), saturated NaHCO$_3$, brine and dried over MgSO$_4$. Filtration and evaporation of solvent gives a solid, which is crystallized from isopropyl ether to give the corresponding title tosylate.

V.

[1β,2α(5Z),3α,4β]-7-[(3-(Aminomethyl)-7-thiabicyclo[2.2.1]hept-2-yl]-5-heptenoic acid, methyl ester The title U tosylate is subjected to a Gabriel synthesis to form the corresponding amino compound as described below.

The potassium phthalimide used is purified prior to use by boiling 5 g thereof with 9 ml acetone for 15 minutes, filtering while hot and washing with 5 ml acetone. The remaining solid is dried in vacuo for 6 hours at 100° C. prior to use.

The title B tosylate (19.2 mmol) and purified potassium phthalimide (6.4 g, 34.6 mmol, 1.8 equiv.) in dimethylsulfoxide (70 ml, Burdick & Jackson) are heated at 90°–100° C. for 2½ hours (checked by TLC Et$_2$O-pet ether 2:1, no tosylate remaining). After cooling to room temperature, water (90 ml) is added. The mixture is poured into ice water (~350 ml) and stirred 30 minutes. The straw colored solid is harvested by filtration and washed with more water. The solid is dissolved in warm ethyl acetate (150 ml), washed with water (3×50 ml), dried (MgSO$_4$), filtered and freed of solvent in vacuo. The remaining solid is recrystallized from isopropyl ether (~150 ml) to give corresponding phthalimide (13.8 mmol) is dissolved in distilled CH$_2$Cl$_2$ (24 ml) and distilled ethanol (104 ml) in an argon atmosphere. Anhydrous hydrazine (0.78 ml, 25.6 mmol) is added. The mixture is stirred at room temperature. After 8 hours an additional 0.2 ml of hydrazine is added and the mixture is stirred an additional 15 hours at room temperature. A solid is removed by filtration and washed with more CH$_2$Cl$_2$. The filtrate is taken to dryness in vacuo (on the pump at end). Cold 0.5N HCl solution (80 ml) is added. The acidic solution is washed with ether (2×100 ml) and then basified with solid K$_2$CO$_3$. The amine is extracted into CHCl$_3$ (3×100 ml), dried (MgSO$_4$) and freed of solvent in vacuo leaving an oil. Ether (100 ml) is added to this oil. After cooling in an ice bath, the solid is removed by filtration. The solvent is removed from the filtrate in vacuo leaving title amine. The material is used without further purification.

W.

[1β,2α(5Z),3α,4β]-7-[3-[[[[(1-Oxohexyl)amino]acetyl]amino]methyl]-7-thiabicyclo[2.2.1]hept-2-yl]-5-heptenoic acid, methyl ester Part T compound (1.5 mmol) is dissolved in distilled THF (12 ml) in an argon atmosphere. After cooling in an ice bath carbonyldiimidazole (CDI) (243 mg, 1.5 mmol) is added. The mixture is stirred cold for 1 hour and then at room temperature for 1 hour. The solution is cooled to 0° C. and a solution of Part V amine (1.5 mmol) in THF (3 ml) is added. The mixture is left stirring overnight at room temperature. The solvent is removed in vacuo and the residue is dissovled in CHCl$_3$ (50 ml). This is washed with 1N HCl (20 ml), 1N NaOH (20 ml) and H$_2$O (20 ml), dried (MgSO$_4$) and freed of solvent in vacuo leaving a viscous oil. The oil is chromatographed on silica gel (Baker for flash chromatography), eluting with EtOAc and 1% MeOH in EtOAc to give title compound.

EXAMPLE 2

[1β,2α(5Z),3α,4β]-7-[3-[[[[(1-Oxohexyl)amino]-acetyl]amino]methyl]-7-thiabicyclo[2.2.1]hept-2-yl]-5-heptenoic acid The Example 1 methyl ester (0.994 mmol) is dissolved in distilled THF (40 ml) and water (8 ml) in an argon atmosphere. 1N LiOH solution (9.5 ml) is added and the mixture is stirred at room temperature for 3¾ hours. After neutralization with 1N HCl (9.5 ml), solid KCl is added and the layers are separated. The aqueous layer is reextracted with CHCl$_3$ (3×50 ml). The combined organic layers (THF+CHCl$_3$) are washed with saturated NaCl solution (2×25 ml), dried (MgSO$_4$), and freed of solvent in vacuo leaving a viscous oil. This is chromatographed on silica gel (Baker for flash chromatography) eluting with 4% MeOH in CH$_2$Cl$_2$ to give material which crystallizes. This is recrystallized from acetonitrile (~10 ml) to give title acid.

EXAMPLE 3

[1β,2α(5Z),3α,4β]-7-[3-[[[[[(Butylamino)-carbonyl]amino]acetyl]methyl]-7-thiabicyclo[2.2.1]hept-2-yl]-5-heptenoic acid, methyl ester A. N-[(Butylamino)carbonyl]glycine, ethyl ester Glycine ethyl ester.HCl (5.58 g, 40 mmol) was suspended in distilled CH$_2$Cl$_2$ (20 ml). After cooling in an ice bath, distilled Et$_3$N (6.13 ml, 44 mmol) was added. Distilled n-butyl isocyanate (4.95 ml, 44 mmol) was added. The cooling bath was removed and the mixture was left stirring overnight at room temperature. Additional Et$_3$N (3.05 ml) was added and the mixture was stirred 3 more hours. After diluting with more CH$_2$Cl$_2$, the solution was washed with water (50 ml), 1N HCl (50 ml), saturated NaHCO$_3$ solution (50 ml) and water (50 ml). After drying (MgSO$_4$), the solvent was removed in vacuo leaving the title compound (7.641 g, 94%) which slowly crystallized. This was used without further purification.

B. N-[(Butylamino)carbonyl]glycine

Part A ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried (MgSO$_4$), and freed of solvent in vacuo leaving the title compound, as a white solid (2.81 g, 97%).

C. [1β,2α(5Z),3α,4β]-7-[3-[[[[[(Butylamino)carbonyl]amino]acetyl]amino]-methyl]-7-thiabicyclo[2.2.1]hept-2-yl]-5-heptenoic acid, methyl ester Part B compound (174.2 mg, 1 mmol) is partially dissolved in distilled THF (8 ml) in an argon atmosphere. After cooling in an ice bath, carbonyl diimidazole (CDI) (162 mg, 1 mmol) is added. The mixture is stirred cold 1 hour and at room temperature 1½ hours (became a clear solution near the end of this time). The solution is cooled in an ice bath and a solution of amine prepared in Example 1 Part V (1 mmol) in THF (3 ml) is added. The cooling bath is removed and the mixture is left stirring overnight at room temperature. The solvent is removed in vacuo. CHCl$_3$ (35 ml) is added to the residue. The solution is washed with 1N HCl (15 ml), 1N NaOH (15 ml) and H$_2$O (15 ml), dried (MgSO$_4$) and freed of solvent in vacuo leaving a viscous oil. This is chromatographed on silica gel (Baker for flash chromatography), eluting with EtOAc and 5% MeOH in EtOAc to give the title compound.

EXAMPLE 4

[1β,2α(5Z),3α,4β]-7-[3-[[[[[(Butylamino)carbonyl]amino]acetyl]amino]methyl]-7-thiabicyclo[2.2.1]hept-2-yl]-5-heptenoic acid Example 3 methyl ester (0.491 mmol) is dissolved in distilled THF (20 ml) and water (4.8 ml) in an argon atmosphere. 1N LiOH solution (4.9 ml) is added and the mixture is stirred at room temperature 5 hours. The mixture is neutralized with 1N HCl solution (4.9 ml) and solid KCl is added. The layers are separated. The aqueous layer is reextracted with CHCl$_3$ (3×25 ml). The combined organic layer (THF and CHCl$_3$) are washed with saturated NaCl solution (15 ml), dried (MgSO$_4$) and freed of solvent in vacuo leaving an oil. This is chromatographed on silica gel (18 g), eluting with 4% MeOH in CH$_2$Cl$_2$ to give the title compound.

EXAMPLE 5

[1β,2α(5Z),3α,4β]-7-[3-[[[[Methyl(1-oxohexyl)amino]acetyl]amino]methyl]-7-thiabicyclo[2.2.1]-hept-2-yl]-5-heptenoic acid, methyl ester

A. N-Hexanoyl-N-methylglycine

Sarcosine (1.78 g, 20 mmol) was dissolved in 1N NaOH solution (40 ml) and Et$_2$O (40 ml) was added. After cooling in an ice bath a solution of hexanoyl chloride (3.1 ml, 22 mmol) in Et$_2$O (10 ml) was added dropwise. The mixture was stirred cold for 1 hour. The pH was then adjusted to about 8 by adding 1N NaOH solution (about 3 ml) and the mixture was stirred at room temperature 45 minutes. NaOH solution was added to about pH 9–10. The layers were separated and the aqueous layer was washed with Et$_2$O (50 ml). After acidification of the aqueous layer with concentrated HCl and saturation with solid KCl, the product was extracted into CHCl$_3$ (3×70 ml). The combined CHCl$_3$ extracts were washed with saturated NaCl solution (25 ml), dried (MgSO$_4$), and freed of solvent leaving the title compound as an oil (3.78 g, quant.) which was used without further purification.

B. [1β,2α(5Z),3α,4β]-7-[3-[[[[Methyl(1-oxohexyl)amino]acetyl]amino]methyl]-7-thiabicyclo[2.2.1]hept-2-yl]-5-heptenoic acid, methyl ester Part A compound (187 mg, 1 mmol) is dissolved in distilled THF (8 ml) in an argon atmosphere and cooled in an ice bath. Carbonyldiimidazole (CDI) (162 mg, 1 mmol) is added and the mixture is stirred cold for 1 hour and then for 1 hour at room temperature. After cooling in an ice bath, a solution of amine prepared in Example 1 part V (1 mmol) in THF (3 ml) is added. The ice bath is removed and the mixture is stirred overnight at room temperature. The solvent is removed in vacuo. CHCl$_3$ (35 ml) is added to the residue. The solution is washed with 1N HCl (15 ml), 1N NaOH solution (15 ml) and H$_2$O (15 ml), dried (MgSO$_4$) and freed of solvent in vacuo leaving an oil. This is chromatographed on silica gel (Baker for flash chromatography), eluting with EtOAc and 2% MeOH in EtOAc to give the title compound.

EXAMPLE 6

[1β,2α(5Z),3α,4β]-7-[3-[[[[Methyl(1-oxohexyl)amino]acetyl]amino]methyl]-7-thiabicyclo[2.2.1]-hept-2-yl]-5-heptenoic acid The Example 5 methyl ester (0.568 mmol) is dissolved in distilled THF (25 ml) and water (5 ml) in an argon atmosphere. 1N LiOH solution is added and the mixture is stirred at room temperature 4 hours. After neutralizing with 1N HCl solution (5.6 ml) and addition of solid KCl, the layers are separated. The aqueous layer is extracted with CHCl$_3$ (3×25 ml). The combined organic layers (THF+CHCl$_3$) are washed with saturated NaCl solution (15 ml), dried (MgSO$_4$) and freed of solvent in vacuo leaving an oil. This is chromatographed on silica gel (Baker for flash chromatography) eluting with 4% MeOH in CH$_2$Cl$_2$ to give the title compound.

EXAMPLE 7

[1β,2α(5Z),3α,4β]-7-[3-[[[[(Butoxycarbonyl)amino]acetyl]amino]methyl]-7-thiabicyclo[2.2.1]-hept-2-yl]-5-heptenoic acid, methyl ester

A. N-(Butoxycarbonyl)glycine ethyl ester

Glycine ethyl ester.HCl (3.5 g, 25 mmol) was suspended in distilled CH$_2$Cl$_2$ (25 ml) in an argon atmosphere. After cooling to −40° C. distilled Et$_3$N (7.65 ml, 55 mmol) was added followed by dropwise addition of a solution of distilled n-butyl chloroformate (3.2 ml, ~25 mmol) in CH$_2$Cl$_2$ (10 ml). After stirring at −40° for 1 hour the mixture was left in a freezer (−5° C.) overnight. The mixture was stirred at −5° to −10° for 1 hour. More CH$_2$Cl$_2$ was added followed by water (50 ml). The layers were separated. The organic layer was washed with 1N HCl (50 ml), saturated NaHCO$_3$ solution (50 ml) and water (50 ml), dried (MgSO$_4$), and freed of solvent in vacuo leaving 3.129 g of material. This was combined with material from a 5 mmol run and chromatographed on silica gel (Baker for flash chromatography), eluting with ether-hexane 1:1 to give the title compound as an oil (3.196 g, 52.5%). TLC: silica gel, Et$_2$O-hexane 1:1, PMA, R$_f$=0.34.

B. N-(Butoxycarbonyl)glycine

The ethyl ester prepared in part A (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried (MgSO$_4$) and freed of solvent in vacuo leaving the title compound (2.78 g, quant.) which slowly crystallized.

C. [1β,2α(5Z),3α,4β]-7-[3-[[[[(Butoxycarbonyl-)amino]acetyl]amino]methyl]-7-thiabicyclo[2.2.1]hept-2-yl]-5-heptenoic acid, methyl ester The acid prepared in part B (1 mmol) is dissolved in distilled THF (8 ml) in an argon atmosphere. After cooling in an ice bath carbonyldiimidazole (CDI) (162 mg, 1 mmol) is added. The mixture is stirred cold 1 hour and at room temperature 1 hour. The mixture is again cooled in an ice bath and a solution of amine (prepared in Example 1 part V, (1 mmol) in THF (3 ml) is added. The cooling bath is removed and the mixture is left stirring overnight at room temperature. The solvent is removed in vacuo. CHCl$_3$ (35 ml) is added. The solution is washed with 1N HCl (15 ml), 1N NaOH (15 ml) and H$_2$O (15 ml), dried (MgSO$_4$) and freed of solvent in vacuo. The remaining oil is chromatographed on silica gel (Baker for flash chromatography) eluting with EtOAc to give partially purified material. This is re-chromatographed on silica gel, eluting with Et$_2$O and 2% MeOH in Et$_2$O to give the title compound.

EXAMPLE 8

[1β,2α(5Z),3α,4β]-7-[3-[[[[(Butoxycarbonyl)-amino]acetyl]amino]methyl]-7-thiabicyclo[2.2.1]hept-2-yl]-5-heptenoic acid The methyl ester prepared in Example 7 (0.396 mmol) is dissolved in distilled THF (16 ml) and water (3.8 ml) in an argon atmosphere and 1N LiOH solution (3.9 ml) is added. The mixture is stirred at room temperature 5½ hours, then neutralized with 1N HCl solution (3.8 ml). After adding solid KCl the layers are separated. The aqueous layer is reextracted with CHCl$_3$ (3×25 ml). The combined organic layers (THF+CHCl$_3$) are washed with saturated NaCl solution (15 ml), dried (MgSO$_4$) and freed of solvent in vacuo leaving an oil. This is chromatographed on silica gel (Baker for flash chromatography) eluting with 4% MeOH in CH$_2$Cl$_2$ to give the title compound.

EXAMPLE 9

[1β,2α(5Z),3α,4β]-N-Methyl-7-[3-[[[[(1-Oxohexyl-)amino]acetyl]amino]methyl]-7-thiabicyclo[2.2.1]hept-2-yl]-5-heptenamide 40% MeNH$_2$ in H$_2$O (2 ml) is added to a magnetically stirred solution of ester prepared in Example 1 (150 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 10

[1β,2α(5Z),3α(R),4β]-7-[3-[[[1-Oxo-2-[(1-Oxohexyl-)amino]propyl]amino]methyl]-7-thiabicyclo[2.2.1]hept-2-yl]-5-heptenoic acid, methyl ester A. (2R)-2-(Hexanoylamino)propionic acid D-alanine (20 mmol) and hexanoyl chloride (22 mmol) were reacted using the method as described in Example 5 Part A to give the title compound as a white crystalline material (2.45 g, 65.5%) after recrystallization from isopropyl ether (20 ml), m.p. 82°-95° C.

B. [1β,2α(5Z),3α(R),4β]-7-[3-[[[1-Oxo-2-[(1-Oxohexyl-)amino]propyl]amino]methyl]-7-thiabicyclo[2.2.1]hept-2-yl]-5-heptenoic acid, methyl ester Part A acid compound (1 mmol) and chiral amine prepared as described in Example 1 Part V (1 mmol) are coupled using CDI (1 mmol) as described in Example 5 Part B. The crude product is chromatographed on silica gel (Baker for flash chromatography) eluting with 2-4% MeOH in Et$_2$O. The eluted product is triturated with Et$_2$O to give the title methyl ester.

EXAMPLE 11

[1β,2α(5Z),3α(R),4β]-7-[3-[[[1-Oxo-2-[(1-Oxohexyl-)amino]propyl]amino]methyl]-7-thiabicyclo[2.2.1]hept-2-yl]-5-heptenoic acid The Example 10 methyl ester (0.49 mmol) is hydrolyzed with LiOH solution in a THF-water mixture as described in Example 6. The viscous product is dissolved in EtOAc. On standing crystalline material is deposited. This is harvested by filtration and washed with Et$_2$O to give title acid.

EXAMPLE 12

[1β,2α(5Z),3α(S),4β]-7-[3-[[[1-Oxo-2-[(1-oxohexyl-)amino]propyl]amino]methyl]-7-thiabicyclo[2.2.1]hept-2-yl]-5heptenoic acid, methyl ester A. (2S)-2-(Hexanoylamino)propionic acid L-Alanine (10 mmol) and hexanoyl chloride (11 mmol) were reacted using the method described in Example 5 Part A to give the title compound as a white crystalline material (1.091 g, 58%) after recrystallization from isopropyl ether (~6 ml).

B. [1β,2α(5Z),3α(S),4β]-7-[3-[[[1-Oxo-2-[(1-oxohexyl-)amino]propyl]amino]methyl]-7-thiabicyclo[2.2.1]hept-2-yl]-5-heptenoic acid, methyl ester Part A compound (1 mmol) and amine (prepared as described in Example 1 Part V) (1 mmol) are coupled using CDI (1 mmol) as described in Example 5 Part B. The crude product is chromatographed on silica gel (Baker for flash chromatography) eluting with 2% MeOH in Et$_2$O to give title methyl ester.

EXAMPLE 13

[1β,2α(5Z),3α(S),4β]-7-[3-[[[1-Oxo-2-[(1-oxohexyl-)amino]propyl]amino]methyl]-7-thiabicyclo[2.2.1]hept-2-yl]-5-heptenoic acid The Example 12 methyl ester (0.40 mmol) is hydrolyzed with LiOH in a THF-water mixture as described in Example 6. The viscous product is dissolved in EtOAc. Crystalline material is deposited on standing. This is harvested by filtration and washed with cold Et₂O to give the title compound.

EXAMPLE 14

[1β,2α(5Z),3α,4β]-7-[3-[[[2-Methyl-2-[(1-Oxohexyl)amino]-1-oxopropyl]amino]methyl]-7-thiabicyclo[2.2.1]hept-2-yl]-5-heptenoic acid, methyl ester

A. 2-(Hexanoylamino)-2-methylpropionic acid

2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 5, Part A. The title compound (1.90 g, 49%) was obtained after crystallization from benzene, m.p. 141°-143° C.

B.
[1β,2α(5Z),3α,4β]-7-[3-[[[2-Methyl-2-[(1-Oxohexyl)amino]-1-oxopropyl]amino]methyl]-7-thiabicyclo[2.2.1]hept-2-yl]-5-heptenoic acid, methyl ester Part A compound (1 mmol) is reacted with CDI (1 mmol) and then with amine prepared as described in Example 1 Part V (1 mmol) employing the method described in Example 1 Part W. The crude product is chromatograhed on silica gel (Baker for flash chromatography), eluting with 2% MeOH in Et₂O to give title ester.

EXAMPLE 15

[1β,2α(5Z),3α,4β]-7-[3-[[[2-Methyl-2-[(1-oxohexyl)amino]-1-oxopropyl]amino]methyl]-7-thiabicyclo[2.2.1]hept-2-yl]-5-heptenoic acid The Example 14 methyl ester (0.51 mmol) is hydrolyzed with LiOH in a water-THF mixture as described in Example 6. The product is crystallized from ethyl acetate to give title acid.

EXAMPLE 16

[1β,2α(5Z),3α,4α]-7-[3-[[[[(1-Oxoheptyl)amino]acetyl]amino]methyl]-7-thiabicyclo[2.2.1]hept-2-yl]-5-heptenoic acid, methyl ester

A. 2-(Heptanoylamino)acetic acid

Glycine (1.5 g, 20 mmol) and heptanoyl chloride (22 mmol) were reacted in the presence of NaOH (40 mmol) in a mixture of water and ether using the method described in Example 5. The crude product was recrystallized from EtOAc (30 ml) to give title compound (2.71 g, 72%), m.p. 98°-100° C.

B.
[1β,2α(5Z),3α,4α]-7-[3-[[[[(1-Oxoheptyl)amino]acetyl]amino]methyl]-7-thiabicyclo[2.2.1]hept-2-yl]-5-heptenoic acid, methyl ester Part A compound (1 mmol) is reacted with CDI (1 mmol) and then with amine (1 mmole) prepared as described in Example 1 Part V employing the method described in Example 5 Part B. The crude product is chromatographed on silica gel (Baker for flash chromatography) eluting with EtOAc and 2% MeOH in EtOAc to give title ester.

EXAMPLE 17

[1β,2α(5Z),3α,4β]-7-[3-[[[[(1-Oxoheptyl)amino]acetyl]amino]methyl]-7-thiabicyclo[2.2.1]hept-2-yl]-5-heptenoic acid The Example 16 methyl ester (0.607 mmol) is hydrolyzed with LiOH in a water-THF mixture as described in Example 6. The crude crystalline product is recrystallized from EtOAc (4 ml) to give title acid.

EXAMPLE 18

(1β,2α,3α,4β)-7-[3-[[[[(1-Oxohexyl)amino]acetyl]amino]methyl]-7-thiabicyclo[2.2.1]hept-2-yl]heptanoic acid, methyl ester

A.
(1β,2α,3α,4β)-7-[3-Hydroxymethyl)-7-thiabicyclo[2.2.1]hept-2-yl]heptanoic acid, methyl ester To 3.0 mmole of [1β,2α(Z),3α,4β]-7-[3-(hydroxymethyl)-7-thiabicyclo[2.2.1]hept-2-yl]-5-heptenoic acid, methyl ester dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a Celite plug and evaporated to provide title A compound.

B.
(1β,2α,3α,4β)-7-[3-[[[[(1-Oxohexyl)amino]acetyl]amino]methyl]-7-thiabicyclo[2.2.1]hept-2-yl]heptanoic acid, methyl ester Following the procedure of Example 1 except substituting the Part A alcohol-ester for the alcohol ester employing in Example 1 Part U, the title product is obtained.

EXAMPLE 19

[1β,2α(5Z),3α,4β]-7-[3-[[[(1-Oxo-3-[(1-oxopentyl)amino]propyl]amino]methyl]-7-thiabicyclo[2.2.1]hept-2-yl]-5-heptenoic acid

A. 3-(Pentanoylamino)propionic acid

β-Alanine (20 mmol) was reacted with valeryl chloride (22 mmol) in the presence of NaOH (40 mmol) in a mixture of H₂0 and ether using the method described in Example 5. The crude crystalline product (2.75 g, 79%) was recrystallized from a mixture of isopropyl ether (150 ml) and ethyl acetate (10 ml) to give title acid (1.51 g, 44%), m.p. 73°-76° C.

B.
[1β,2α(5Z),3α,4β]-7-[3-[[[(1-Oxo-3-[(1-oxopentyl)amino]propyl]amino]methyl]-7-thiabicyclo[2.2.1]hept-2-yl]-5-heptenoic acid, methyl ester Part A acid (1 mmol) is reacted with carbonyl diimidazole (1 mmol) followed by [1β,2α(5Z),3α,4β]-7-[3-(aminomethyl)-7-thiabicyclo[2.2.1]hept-2-yl]-5-heptenoic acid, methyl ester (prepared as described in Example 1 Part V (1 mmole)). The crude product is chromatographed on silica gel (Baker for flash chromatography) eluting with 5-10% MeOH in Et₂O to give title product.

C.
[1β,2α(5Z),3α,4β]-7-[3-[[[1-Oxo-3-[(1-oxopentyl)amino]propyl]amino]methyl]-7-thiabicyclo[2.2.1]hept-2-yl]-5-heptenoic acid The Part B methyl ester (0.71 mmol) is hydrolyzed with LiOH in a THF-H$_2$O mixture as described in Example 6 to give a white solid. This is recrystallized from EtOAc to give title acid.

EXAMPLE 20

[1β,2α(5Z),3α,4β]-7-[3-[[[[(4-Phenylbenzoyl)amino]acetyl]amino]methyl]-7-thiabicyclo[2.2.1]hept-2-yl]-5-heptenoic acid

A. 2-[(4-Phenylbenzoyl)amino]acetic acid

Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in CHCl$_3$ and EtOAc. It was largely dissolved in CH$_3$CN (~35 ml) and filtered to remove insoluble material. Crystalline acid (0.81 g, 63%) was deposited on cooling, m.p. 207°–218° C. decomp.

B.
[1β,2α(5Z),3α,4β]-7-[3-[[[[(4-Phenylbenzoyl)amino]acetyl]amino]methyl]-7-thiabicyclo[2.2.1]hept-2-yl]-5-heptenoic acid, methyl ester Part A acid (1 mmol) is reacted with carbonyldiimidazole (1 mmole) followed by [1β,2α(5Z),3α,4β]-7-[3-aminomethyl)-7-oxabicyclo[2.2.1]hept-2-yl]-5-heptenoic acid, methyl ester (1 mmole) as in Example 1, Part V. After stirring overnight at room temperature. DMF (3 ml) is added and the mixture is left stirring an additional 24 hours. After the usual work up, the viscous product is chromatographed on silica gel (Baker for flash chromatography), eluting with 2% MeOH in CH$_2$Cl$_2$. The material obtained from the column is crystallized from ethyl acetate (2 ml) to give title ester.

C.
[1β,2α(5Z),3α,4β]-7-[3-[[[[(4-Phenylbenzoyl)amino]acetyl]amino]methyl]-7-thiabicyclo[2.2.1]hept-2-yl]-5-heptenoic acid The Part B methyl ester (0.279 mmol) is hydrolyzed with LiOH as described in Example 6 to give a white solid. This is triturated with EtOAc to give title acid.

EXAMPLE 21

[1β,2α(5Z),3α,4β]-7-[3-[2-[[[(1-Oxohexyl)amino]acetyl]amino]ethyl]-7-thiabicyclo[2.2.1]hept-2-yl]-5-heptenoic acid

A.
[1β,2α(Z),3α,4β]-7-[3-(2-Oxo)ethyl-7-thiabicyclo[2.2.1]hept-2-yl]-5-heptenoic acid, methyl ester Into a dry 100 ml round bottom 3-necked flask containing a stir bar is added dried 12.9 g (37.7 mmoles) methoxymethyltriphenylphosphonium chloride ((C$_6$H$_5$)$_3$P$^+$—CH$_2$OCH$_3$Cl$^-$) and 235 ml distilled toluene (stored over molecular sieves). The resulting suspension is stirred in an ice-bath, under argon, until cold and than a 1.55 M solution of 18.3 ml (28.3 mmol) of potassium t-amylate in toluene is added dropwise. A bright red solution forms which is stirred at 0° C. for an additional 35 minutes. Thereafter, a solution of (18.8 mmol) [1β,2α(5Z),3α,4β]-7-[3-formyl-7-thiabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated NH$_4$Cl, and extracted with ether (4×200 ml). The combined ether phases are washed with NaCl, saturated solution, and dried (MgSO$_4$) and concentrated to yield a solid (phosphine oxide). The white solid is triturated with EtOAc and the mother liquor is purified by chromatography on an LPS-1 silica column. The fractions obtained are (A) [1β,2α(Z),3α,4β]-7-[3-(2-oxo)ethyl-7-thiabicyclo[2.2.1]hept-2-yl]-5-heptenoic acid, methyl ester, (B) [1β,2α(Z),3α,4β]-7-[3-(2-methoxy)-ethenyl-7-thiabicyclo[2.2.1]hept-2-yl]-5-heptenoic acid, methyl ester, and (C) [1β,2α(Z),3α,4β]-7-[3-(2,2-dimethoxy)ethyl-7-thiabicyclo[2.2.1]hept-2-yl]-5-heptenoic acid, methyl ester.

Compounds (B) and (C) are each treated with trifluoroacetic acid to convert each to compound (A).

B.
[1β,2α(5Z),3α,4β]-7-[3-(2-Hydroxyethyl)-7-thiabicyclo[2.2.1]hept-2-yl]-5-heptenoic acid, methyl ester The aldehyde (5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.
[1β,2α(Z),3α,4β]-7-[3-[2-[[[(1-Oxohexyl)amino]acetyl]amino]ethyl]-7-thiabicyclo[2.2.1]hept-2-yl]-5-heptenoic acid Following the procedure of Examples 1 and 2 except substituting the above part B alcohol for the alcohol used in Example 1 Part U, the title compound is obtained.

EXAMPLE 22

[1β,2α(5Z),3α,4β]-7-[4-[[[(1-Oxohexyl)amino]acetyl]amino]butyl]-7-thiabicyclo[2.2.1]hept-2-yl]-5-heptenoic acid

A.
[1β,2α(5Z),3α,4β]-7-[3-(3-Oxo)-propyl-7-thiabicyclo[2.2.1]hept-2-yl]-5-heptenoic acid, methyl ester Following the procedure of Example 21 Part A except substituting [1β,2α(Z),3α,4β]-7-[3-(2-oxo)-ethyl-7-thiabicyclo[2.2.1]hept-2-yl]-5-heptenoic acid, methyl ester for [1β,2α(Z),3α,4β]-7-[3-formyl-7-thiabicyclo[2.2.1]hept-2-yl]-5-heptenoic acid, methyl ester, the title A compound is obtained.

B.
[1β,2α(Z),3α,4β]-7-[3-(4-Oxo)-butyl-7-thiabicyclo[2.2.1]hept-2-yl]-5-heptenoic acid, methyl ester Following the procedure of Example 20 Part A except substituting the aldehyde from Part A above for [1β,2α(Z),3α,4β]-7-[3-formyl-7-thiabicyclo[2.2.1]hept- 2-yl]-5-heptenoic acid, methyl ester, the title B compound is obtained.

C.
[1β,2α(Z),3α,4β]-7-[3-(4-Hydroxybutyl)-7-thiabicyclo[2.2.1]hept-2-yl]-5-heptenoic acid, methyl ester Following the procedure of Example 20 Part B except substituting the title B aldehyde for [1β,2α(Z),3α,4β]-7-[3-(2-oxo)ethyl-7-thiabicyclo[2.2.1]hept-2-yl]-5-heptenoic acid, methyl ester, the title C alcohol is obtained.

D.
[1β,2α(Z),3α,4β]-7-[3-[4-[[[(1-Oxohexyl)amino]acetyl]amino]butyl]-7-thiabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 23
[1β,2α(5Z),3α,4β]-8-[3-[[[[(1-Oxohexyl)-amino]acetyl]amino]methyl]-7-thiabicyclo[2.2.1]hept-2-yl]-5-octenoic acid

A.
(1β,2α,3α,4β)-3-[3-(Hydroxymethyl)-7-thiabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) is chilled to 0° C. and treated dropwise with 1.4M potassium t-amylate in toluene (1910 ml, 2.67 mol) over 20 minutes. The resultant solution is stirred at 0° C. for 1 hour. The mixture is then treated slowly over 5 minutes with hemiacetal (1.28 mol). The mixture is stirred vigorously at room temperature for 90 minutes. The reaction mixture is then chilled to 0° C. and treated slowly with acetaldehyde (124 ml, 2.2 mol) over 10 minutes. The mixture is diluted with water (2500 ml) and treated with 10% hydrochloric acid to pH 7. The mixture is then extracted with ether (7×2 liters). The combined ether extracts are dried over magnesium sulfate, filtered, and the filtrates concentrated in vacuo. The resultant mixture is treated with isopropyl ether (4 liters) and stirred overnight. The mixture is chilled to −10° C. for 90 minutes then filtered. The solids are washed thoroughly with isopropyl ether. The filtrate is concentrated in vacuo to an oily residue (460 g). This oily residue is treated with water (4000 ml) and stirred vigorously for 2 hours. The aqueous layer is decanted and the oily residue treated two additional times with water (2×1 liter). After the third wash, the residue solidifies and is filtered. The combined aqueous triturates are concentrated in vacuo. The mixture is filtered through a bed of Celite. The filtrate is concentrated again. The cloudy solution is chilled in an ice bath and treated slowly with concentrated hydrochloric acid (683 ml). The mixture is then stirred at room temperature for 3 hours. After this time the solution is neutralized by the slow addition of solid sodium bicarbonate (720 g). The mixture is filtered through a bed of Celite then extracted with hexane (4×2 liters) then ethyl acetate (10×2 liters). The combined ethyl acetate extracts are dried over MgSO₄ and concentrated in vacuo to yield title aldehyde.

B.
[1β,2α(Z),3α,4β]-8-[3-Hydroxymethyl)-7-thiabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution is added a solution of Part A aldehyde (6 mmole) in 20 ml of dimethyl sulfoxide and the resulting mixture stirred at room temperature for 45 minutes. The reaction is quenched by addition of 24 mmole of acetic acid and the mixture poured into brine (300 ml) and extracted with ether (3×200 ml). Concentration of these extracts gives an oil which is stirred with saturated sodium bicarbonate solution until crystalline triphenylphosphine oxide forms in the mixture. This mixture is washed with benzene and acidified with 10% hydrochloric acid. The aqueous layer is saturated with salt and extracted with ether which on drying (sodium sulfate) and concentration gives crude product. The mixture is stirred 24 hours with 10% aqueous sodium hydroxide and reisolated by acidification and ether extraction. The product is purified on silica gel with 50/50 ethyl acetate-hexane as the eluant which gives acid. This is treated with diazomethane (CH₂N₂) in Et₂O to give the title compound.

C.
[1β,2α(Z),3α,4β]-8-[3-[[[[(1-Oxohexyl)amino]acetyl]amino]methyl]-7-thiabicyclo[2.2.1]hept-2-yl]-5-octenoic acid Following the procedure of Examples 1 and 2 except substituting the title B ester for the ester used in Example 1 Part U, the title compound is obtained.

EXAMPLE 24
[1β,2α(Z),3α,4β]-6-[3-[[[(1-Oxohexyl)amino]acetyl]amino]methyl]-7-thiabicyclo[2.2.1]hept-2-yl]-1-(1H-tetrazol-5-yl)-4-hexene

A.
[1β,2α(Z),3α,4β]-6-[3-Hydroxymethyl-7-thiabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and hemi-acetal F is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO₃ solution, washed with 100 ml of ether, acidified with dilute HCl to pH 3, and extracted with three 500 ml portions of ethyl acetate. The combined organic solutions are dried over anhydrous MgSO₄, and purified by silica chromatography using a 5% methanol in methylene chloride eluant to provide title A compound.

B.
[1β,2α(5Z),3α,4β]-6-[3-[[[(1-Oxohexyl)amino]acetyl]amino]methyl]-7-thiabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part U, the title compound is obtained.

EXAMPLE 25

[1β,2α(5Z),3α,4β]-7-[3-[[[[(1-Oxohexyl)amino]acetyl]amino]methyl]-7-thiabicyclo[2.2.1]hept-2-yl]-N-hydroxy-N-methyl-5-heptenamide A solution of Example 2 acid (0.82 mmol) in dry benzene (5.0 ml) is treated with oxalyl chloride (1 ml; 11.24 mmol or 13.7 eq.) and a drop of DMF, and stirred at room temperature under nitrogen for 2 hours. The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 26

[1β,2α(5Z),3α,4β]-7-[3-[[[[(1-Thioxohexyl)amino]acetyl]amino]methyl]-7-thiabicyclo[2.2.1]hept-2-yl]-5-heptenoic acid, methyl ester

A. [(1-Thioxohexyl)amino]acetic acid

(1) Ethyl [(1-oxohexyl)amine]acetate

Glycine ethyl ester hydrochloride (9.52 g, 70 mmol) was added to a cooled mixture of Na$_2$CO$_3$ (7.63 g, 72 mmol) in water (70 ml) and ether (70 ml). A solution of hexanoyl chloride (9.82 ml) in ether (10 ml) was added by fast dropwise addition. The ice bath was removed and the mixture was stirred at room temperature 1 hour. Saturated NaHCO$_3$ solution (50 ml) was added and the layers were separated. The aqueous layer was reextracted with ether (50 ml). The combined ether layers were washed with saturated NaHCO$_3$ solution (50 ml), 1N HCl solution (50 ml) and water (3×50 ml), dried (MgSO$_4$) and freed of solvent in vacuo leaving title intermediate as a straw colored oil (11.24 g, 80%).

(2) Ethyl [(1-thioxohexyl)amino]acetate

Phosphorus (IV) sulfide (5.64 mmol) was suspended in freshly distilled benzene (10 ml) in an argon atmosphere. A solution of the amide (3.78 g, 18.8 mmol, prepared as described in Part (1)) in distilled benzene (5 ml) was added and the mixture was heated at 74°–80° C. for 1 hour and 20 minutes. After cooling to room temperature, ice (about 10 g) was added and the mixture was stirred 10 minutes, then saturated NaHCO$_3$ solution (15 ml) was added and stirring was continued 10 minutes. Ether (50 ml) was added and the layers were separated. The aqueous layer was reextracted with ether (30 ml). The combined ether layers were washed with NaHCO$_3$ solution (10 ml) and water (20 ml), dried (MgSO$_4$), filtered and freed of solvent in vacuo leaving an oil (4.23 g). This was chromatographed on silica gel (145 g, Baker for flash chromatography), eluting with ether-hexane 1:2 to give title (2) intermediate as an oil (1.19 g, 29%). TLC: silica gel ether-hexane 1:1, UV+ PMA, R$_f$=0.39.

(3) [(1-Thioxohexyl)amino]acetic acid

The Part (2) ethyl ester (1.19 g, 5.48 mmol) was treated with a solution of NaOH (3 g, 75 mmol) in water (45 ml). After stirring at room temperature 45 minutes, the mixture was washed with ether (2×50 ml). The aqueous solution was acidified with concentrated HCl and the product was extracted into ether (2×50 ml). The extracts were dried (MgSO$_4$) and freed of solvent in vacuo leaving material which was crystalline. This was recrystallized from benzene to give title (3) acid (596 mg, 58%), m.p. 106°–109° C.

B.
[1β,2α(5Z),3α,4β]-7-[3-[[[[(1-Thioxohexyl)amino]acetyl]amino]methyl]-7-thiabicyclo[2.2.1]hept-2-yl]-5-heptenoic acid, methyl ester Part A acid compound (189 mg, 1 mmol) is dissolved in distilled THF (8 ml) in an argon atmosphere and cooled in an ice bath. Carbonyldiimidazole (CDI, 162 mg, 1 mmol) is added and the mixture is stirred cold for 1 hour and then for 1 hour at room temperature. After cooling in an ice bath, a solution of amine prepared in Example 1 part V (1 mmol) in THF (3 ml) is added. The ice bath is removed and the mixture is stirred overnight at room temperature. The solvent is removed in vacuo. CHCl$_3$ (35 ml) is added to the residue. The solution is washed with 1N HCl (15 ml), 1N NaOH solution (15 ml) and H$_2$O (15 ml), dried (MgSO$_4$) and freed of solvent in vacuo leaving an oil. This is chromatographed on silica gel (Baker for flash chromatography), eluting with ethyl acetate and 2% MeOH in ether to give the title compound.

EXAMPLE 27

[1β,2α(5Z),3α,4β]-7-[3-[[[[(1-Thioxohexyl)amino]acetyl]amino]methyl]-7-thiabicyclo[2.2.1]hept-2-yl]-5-heptenoic acid The Example 26 methyl ester (0.74 mmol) is dissolved in distilled THF (25 ml) and water (5 ml) in an argon atmosphere. 1N LiOH solution is added and the mixture s stirred at room temperature 4 hours. After neutralizing with 1N HCl solution (5.6 ml) and addition of solid KCl, the layers are separated. The aqueous layer is extracted with CHCl$_3$ (3×25 ml). The combined organic layers (THF+CHCl$_3$) are washed with saturated NaCl solution (15 ml), dried (MgSO$_4$) and freed of solvent in vacuo leaving an oil (242 mg). This is chromatographed on silica gel (Baker for flash chromatography) eluting with 2% MeOH in ethyl acetate to give partially crystalline material. This is triturated with Et$_2$O to give a solid. This is recrystallized from ethyl acetate (2–3 ml) to give title acid.

EXAMPLE 28

[1β,2α(5Z),3α,4β]-7-[3-[[[1,3-Dioxo-3-(pentylamino)-propyl]amino]methyl]-7-thiabicyclo[2.2.1]hept-2-yl]-5-heptenoic acid, methyl ester

A. Methyl-3-(pentylamino)-3-oxopropionate

Dimethylmalonate (3.2 g, 24 mmol) and n-amylamine (2.1 g, 24 mmol) were mixed at room temperature. After stirring one hour solid began to precipitate. Diisopropyl ether (10 ml) was added and the mixture was left overnight at room temperature. The reaction mixture was concentrated in vacuo. The residue was chromatographed on silica gel (100 g, Baker for flash chromatography), eluting with $CH_2Cl_2$ and 2% MeOH in $CH_2Cl_2$ to give the title compound as an oil (1.97 g, 44%).

B. 3-Pentylamino-3-oxopropionic acid

Part A compound (1.43 g, 7.6 mmol) was dissolved in methanol (~1 ml) and treated with 1N LiOH solution (20 ml). The heterogeneous solution was left stirring overnight at room temperature. During this time it became homogeneous. The solution was washed with ether (50 ml). The water layer was then acidified with concentrated HCl to pH about 1. The product was extracted into ether (2×50 ml). The combined ether extracts were washed with saturated NaCl solution, dried ($MgSO_4$) and freed of solvent in vacuo to give a solid. This was recrystallized from diisopropyl ether to give the title compound, (1.15 g, 87%), m.p. 67.5°–68.5° C.

C. [1β,2α(5Z),3α,4β]-7-[3-[[[1,3-Dioxo-3-(pentylamino)-propyl]amino]methyl]-7-thiabicyclo[2.2.1]hept-2-yl]-5-heptenoic acid, methyl ester Part B compound (1 mmol) is dissolved in distilled THF (8 ml) in an argon atmosphere. After cooling in an ice bath carbonyldiimidazole (CDI) (162 mg, 1 mmol) is added. The mixture is stirred cold for 1 hour and then at room temperature for 1 hour. The solution is cooled to 0° C. and a solution of Example 1 Part V amine (1 mmol) in THF (3 ml) is added. The cooling bath was removed and the mixture is left stirring overnight at room temperature. The solvent is removed in vacuo and the residue is dissolved in $CHCl_3$ (50 ml). This is washed with 1N HCl (15 ml), 1N NaOH (15 ml) and saturated NaCl solution (15 ml), dried ($MgSO_4$) and freed of solvent in vacuo leaving an oil. The oil is chromatographed on silica gel (Baker for flash chromatography), eluting with EtOAc and 2% MeOH in EtOAc to give title compound.

EXAMPLE 29

[1β,2α(5Z),3α,4β]-7-[3-[[[1,3-Dioxo-3-(pentylamino)-propyl]amino]methyl]-7-thiabicyclo[2.2.1]hept-2-yl]-5-heptenoic acid The Example 28 methyl ester (0.59 mmol) is dissolved in distilled THF (25 ml) and water (5 ml) in an argon atmosphere. 1N LiOH solution (5.6 ml) is added and the mixture is stirred at room temperature for 4 hours. After neutralization with 1N HCl, solid KCl is added and the layers are separated. The aqueous layer is reextracted with $CHCl_3$ (3×25 ml). The combined organic layers (THF+$CHCl_3$) are washed with saturated NaCl solution (15 ml), dried ($MgSO_4$), and freed of solvent in vacuo leaving an oil. This is chromatographed on silica gel (Baker for flash chromatography) eluting with 4% MeOH in $CH_2Cl_2$ to give an oil which crystallizes on standing. This is triturated with ether to give title acid.

EXAMPLE 30

[1β,2α(5Z),3α,4β]-7-[3-[[[(1-Oxo-3-(pentylamino)-3-thioxopropyl]amino]methyl]-7-thiabicyclo[2.2.1]hept-2-yl]-5-heptenoic acid, methyl ester

A. 3-Pentylamine-3-thioxopropionic acid

(1) Methyl 3-pentylamino-3-oxopropionate

Dimethyl malonate (3.2 g, 24 mmol) and n-amylamine (2.1 g, 24 mmol) were mixed at room temperature. After stirring one hour solid began to precipitate. Diisopropyl ether (10 ml) was added and the mixture was left overnight at room temperature. The reaction mixture was concentrated in vacuo. The residue was chromatographed on silica gel (100 g, Baker for flash chromatography), eluting with $CH_2Cl_2$ and 2% MeOH in $CH_2Cl_2$ to give the title compound as an oil (1.97 g, 44%).

(2) Methyl 3-pentylamino-3-thioxopropionate

Phosphorus (IV) sulfide (1.26 g, 2.8 mmol) was suspended in freshly distilled benzene (10 ml) in an argon atmosphere. A solution of methyl 3-(pentylamino)-3-oxopropionate (1.76 g, 9.4 mmol, prepared as described in Part (1)) in distilled benzene (5 ml) was added and the mixture was heated at 75°–80° C. for 1 hour 20 minutes. After cooling to room temperature, ice (~10 g) was added and the mixture was stirred 10 minutes, then saturated $NaHCO_3$ solution (15 ml) was added and stirring was continued 10 minutes. Ether (50 ml) was added and the layers were separated. The aqueous layer was reextracted with ether (30 ml). The combined ether layers were washed with $NaHCO_3$ solution (10 ml) and water (20 ml), dried ($MgSO_4$), filtered and freed of solvent in vacuo leaving a dark reddish oil (1.773 g). This was chromatographed on silica gel (50 g, Baker for flash chromatography) eluting with ether-hexane 1:2 to give title (2) reactant intermediate as a red orange oil (1.275 g, 67%). TLC: silica gel ether-hexane 1:1, UV and $I_2$, $R_f$ 0.47.

(3) 3-Pentylamino-3-thioxopropionic acid

The Part (2) methyl ester (1.27 g, 6.26 mmol) was treated with a solution of NaOH (3 g, 75 mmol) in water (45 ml). After stirring at room temperature 45 minutes, the mixture was washed with ether (2×50 ml). The aqueous solution was acidified with concentrated HCl and the product was extracted into ether (2×50 ml). The extracts were dried ($MgSO_4$) and freed of solvent in vacuo leaving material which was crystalline. This was recrystallized from a benzene-hexane mixture to give title reactant as pale straw colored crystals (0.90 g, 76%), m.p. 72°–76° C.

B. [1β,2α(5Z),3α,4β]-7-[3-[[[1-Oxo-3-(pentylamino)-3-thioxopropyl]amino]methyl]-7-thiabicyclo[2.2.1]hept-2-yl]-5-heptenoic acid, methyl ester Part A acid compound (1 mmol) is dissolved in distilled THF (8 ml) in an argon atmosphere and cooled in an ice bath. Carbonyldiimidazole (CDI) (162 mg, 1 mmol) is added and the mixture is stirred cold for 1 hour and then for 1 hour at room temperature. After cooling in an ice bath, a solution of amine prepared in Example 1 part V (1 mmol) in THF (3 ml) is added. The ice bath is removed and the mixture is stirred overnight at room temperature. The solvent is removed in vacuo. CHCl$_3$ (35 ml) is added to the residue. The solution is washed with 1N HCl (15 ml), 1N NaOH solution (15 ml) and H$_2$O (15 ml), dried (MgSO$_4$) and freed of solvent in vacuo leaving an oil. This is chromatographed on silica gel (Baker for flash chromatography), eluting with EtOAc and 2% MeOH in methylene chloride to give the title compound.

EXAMPLE 31

[1β,2α(5Z),3α,4β]-7-[3-[[[1-Oxo-3-(pentylamino)-3-thioxopropyl]amino]methyl]-7-thiabicyclo[2.2.1]hept-2-yl]-5-heptenoic acid The Example 30 methyl ester (0.63 mmol) is dissolved in distilled THF (40 ml) and water (8 ml) in an argon atmosphere. 1N LiOH solution (9.5 ml) is added and the mixture is stirred at room temperature for 3¾ hours. After neutralization with 1N HCl (9.5 ml), solid KCl is added and the layers are separated. The aqueous layer is reextracted with CHCl$_3$ (3×50 ml). The combined organic layers (THF+CHCl$_3$) are washed with saturated NaCl solution (2×25 ml), dried (MgSO$_4$), and freed of solvent in vacuo leaving an oil. This is chromatographed on silica gel (Baker for flash chromatography) eluting with 4% MeOH in CH$_2$Cl$_2$ to give material which crystallizes. This is recrystallized from ethyl acetate (5 ml) to give title acid.

EXAMPLE 32

[1β,2α(5Z),3α,4β]-7-[3-[[[[[(Butylamino)carbonyl]oxy]acetyl]amino]methyl]-7-thiabicyclo[2.2.1]hept-2-yl]-5-heptenoic acid, methyl ester A. [[(Butylamino)carbonyl]oxy]acetic acid (1) [[(Butylamino)carbonyl]oxy]acetic acid, methyl ester Methyl glycolate (1.8 g, 20 mmol) was cooled in an ice bath. Triethylamine (180 μl, ~1.3 mmol) was added followed by n-butyl isocyanate (2.92 ml, 26 mmol). The mixture was stirred cold for 30 minutes and then overnight at room temperature. The triethylamine was removed in vacuo and the crude product was purified on a silica gel column (60 g, Baker for flash chromatography) eluting with 30% ether in petroleum ether to give 3.76 g of pure title ester (99%).

(2) [[(Butylamino)carbonyl]oxy]acetic acid

The ester oil from Part (1) (1.82 g, 9.6 mmol) was treated with 2N NaOH (20 ml). The heterogeneous mixture was stirred vigorously at room temperature and became homogeneous in about 30 minutes. After stirring 4 hours, the reaction was washed with ether (2×30 ml) and the ether washes were reextracted with 2N NaOH solution (10 ml). The combined aqueous layers were acidified to pH 1 with concentrated HCl and the product was extracted into ether (2×30 ml). The combined ether extracts were washed with saturated NaCl solution (2×20 ml), dried (MgSO$_4$) and freed of solvent in vacuo. The crude solid obtained (1.48 g) was recrystallized from benzene to give title acid (1.11 g, 6.3 mmol, 66%) as colorless crystals, m.p. 83°-84°.

B. [1β,2α(5Z),3α,4β]-7-[3-[[[[[(Butylamino)carbonyl]oxo]acetyl]amino]methyl]-7-thiabicyclo[2.2.1]hept-2-yl]-5-heptenoic acid, methyl ester Part A compound (1.5 mmol) is dissolved in distilled THF (12 ml) in an argon atmosphere. After cooling in an ice bath carbonyldiimidazole (CDI) (243.2 mg, 1.5 mmol) is added. The mixture is stirred cold for 1 hour and then at room temperature for 1 hour. The solution is cooled to 0° C. and a solution of Example 1 Part V amine (1.5 mmole) in THF (3 ml) is added. The mixture is left stirring overnight at room temperature. The solvent is removed in vacuo and the residue was dissolved in CHCl$_3$ (50 ml). This is washed with 1N HCl (20 ml), 1N NaOH (20 ml) and H$_2$O (20 ml), dried (MgSO$_4$) and freed of solvent in vacuo leaving a viscous oil. The oil is chromatographed on silica gel (Baker for flash chromatography), eluting with 2% MeOH in ether to give title compound.

EXAMPLE 33

[1β,2α(5Z),3α,4β]-7-[3-[[[[[(Butylamino)carbonyl]oxy]acetyl]amino]methyl]-7-thiabicyclo[2.2.1]hept-2-yl]-5-heptenoic acid The Example 32 methyl ester (0.535 mmol) is dissolved in distilled THF (40 ml) and water (8 ml) in an argon atmosphere. 1N LiOH solution (9.5 ml) is added and the mixture is stirred at room temperature for 80 minutes. After neutralization with 1N HCl (9.5 ml), solid KCl is added and the layers are separated. The aqueous layer is reextracted with CHCl$_3$ (3×50 ml). The combined organic layers (THF+CHCl$_3$) are washed with saturated NaCl solution (2×25 ml), dried (MgSO$_4$), and freed of solvent in vacuo leaving an oil. This is chromatographed on silica gel (Baker for flash chromatography) eluting with 4% MeOH in CH$_2$Cl$_2$ to give title acid.

EXAMPLE 34

[1β,2α(5Z),3α,4β]-7-[3-[[[[(1-Oxohexyl)amino]acetyl]amino]methyl]-7-thiabicyclo[2.2.1]hept-2-yl]-5-heptenol NaBH$_4$ (185 mg) is added to a magnetically stirred solution of ester prepared in Example 1 (1 mmole) at 0° C. After hydrogen evolution has subsided, the reaction is allowed to warm to room temperature and stirred overnight (16 hours). Saturated NH$_4$Cl (10 ml) is added and stirred for 1 hour. Most of MeOH is removed in vacuo and the residue is partitioned between EtOAc (50 ml) and brine (10 ml). The water layer is reextracted with EtOAc (40 ml×2). The combined organic layers are washed with brine (30 ml) and dried over MgSO$_4$. Filtration and evaporation of solvent give a crude product, which is purified by silica gel column. The title compound is thus obtained.

EXAMPLE 35

[1β,2α(5Z),3α,4β]-7-[3-[[[[(1-Oxo-4-phenyl)butyl]amino]acetyl]amino]methyl]-7-thiabicyclo[2.2.1]hept-2-yl]-5-heptenoic acid A. 4-Phenylbutanoyl glycine ethyl ester 4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester.HCl (2.09 g, 15 mmol) and distilled Et₃N (2.1 ml, 15 mmol) were added. The mixture was left stirring overnight at room temperature. After removal of the solvent in vacuo, Et₂O (200 ml) was added. The solution was washed with 1N HCl (70 ml), 0.5N NaOH (70 ml) and saturated NaCl solution (70 ml), dried (MgSO₄) and freed of solvent in vacuo leaving title compound (3.13 g, 84%) as white crystalline material. TLC: silica gel, Et₂O, UV; $R_f$: 0.58.

B. 4-Phenylbutanoyl glycine

The Part A ester (3.07 g, 12.3 mmol) was hydrolyzed with NaOH (5 g, 125 mmol) in water (60 ml). After stirring at room temperature 6 hours, neutral material was removed by washing with Et₂O (2×50 ml). The aqueous solution was then acidified with concentrated HCl solution. The product was extracted into CHCl₃ (3×60 ml), dried (MgSO₄) and freed of solvent in vacuo leaving a white solid. This was recrystallized from EtOAc (10 ml) to give title compound (2.18 g, 80%), m.p. 99°–101° C.

C. [1β,2α(5Z),3α,4β]-7-[3-[[[[(1-Oxo-4-phenyl)butyl]amino]acetyl]amino]methyl]-7-thiabicyclo[2.2.1]hept-2-yl]-5-heptenoic acid, methyl ester Example 35 Part B acid (1 mmol) is reacted with CDI (1 mmol) and then with Example 1 Part C chiral amine (1 mmol) as described in Example 5 Part B. The crude product is chromatographed on silica gel (Baker for flash chromatography) eluting with EtOAc and 2% MeOH in EtOAc to give title compound.

D. [1β,2α(5Z),3α,4β]-7-[3-[[[[(1-Oxo-4-phenyl)butyl]amino]acetyl]amino]methyl]-7-thiabicyclo[2.2.1]hept-2-yl]-5-heptenoic acid The Part C methyl ester (336 mg, 0.71 mmol) is hydrolyzed with LiOH in a water-THF mixture as described in Example 6 The crude crystalline product (300 mg) is recrystallized from a mixture of MeOH and EtOAc to give title compound.

EXAMPLE 36

[1α,2β(Z),3β,4α]-7-[3-[[[[(Phenylthio)acetyl]amino]acetyl]amino]methyl]-7-thiabicyclo[2.2.1]hept-2-yl]-5-heptenoic acid

A. (Phenylthio)acetyl glycine ethyl ester

The title ethyl ester was prepared from thiophenoxy acetic acid (15 mmol) and the ethyl ester of glycine.HCl using carbonyldiimidazole (CDI) as described in Example 35, Part A giving 2.95 g (78%) of solid.

B. (Phenylthio)acetyl glycine

The Part A ethyl ester was hydrolyzed with aqueous NaOH as described in Example 35 Part B to give the title acid (1.041 g, 92%) as a crystalline material.

C. [1α,2β(Z),3β,4α]-7-[3-[[[[(Phenylthio)acetyl]amino]acetyl]amino]methyl]-7-thiabicyclo[2.2.1]hept-2-yl]-5-heptenoic acid, methyl ester The Part B acid (1.5 mmol) is reacted with CDI (1.5 mmol) followed by Example 1 Part V chiral amine (1.5 mmol) as described in Example 5 Part B. The crude product is chromatographed on silica gel (Baker for flash chromatography) eluting with EtOAc and 2% MeOH in EtOAc to give title ester.

D. [1α,2β(Z),3β,4α]-7-3-[[[[(Phenylthio)acetyl]amino]acetyl]amino]methyl]-7-thiabicyclo[2.2.1]hept-2-yl]-5-heptenoic acid The Part C methyl ester (467 mg, 0.98 mmol) is hydrolyzed with 1N LiOH (2 equivalents) as described in Example 6. The crude product is recrystallized from EtOAc (10 ml) to give title acid.

EXAMPLE 37

[1α,2β(Z),3β,4α]-7-[3-[[[[3-(4-Hydroxyphenyl)-1-oxopropyl]amino]acetyl]amino]methyl]-7-thiabicyclo[2.2.1]hept-2-yl]-5-heptenoic acid

A. 3-(4-Hydroxyphenyl)propanoyl glycine ethyl ester 3-(4-Hydroxyphenyl)propionic acid (2.49 g, 15 mmol) was reacted with glycine ethyl ester hydrochloride in the presence of CDI and Et₃N as described in Example 35 Part A. After removal of the solvent the residue was dissolved in CHCl₃ and washed with 1N HCl, saturated NaHCO₃ solution and saturated NaCl solution. After drying (MgSO₄) and removal of the solvent in vacuo crude title ester remained (2.44 g) as a viscous oil. NMR indicated this contained a major impurity but it was used without further purification.

B. 3-(4-Hydroxyphenyl)propanoyl glycine

Crude Part A ethyl ester was hydrolyzed with NaOH in water as described in Example 56 Part B to give a white solid (1.37 g). This was recrystallized from EtOAc.MeOH to give the title solid (0.98 g, 29% from starting acid).

C. [1α,2β(Z),3β,4α]-7-[3-[[[[3-(4-Hydroxyphenyl)-1-oxopropyl]amino]acetyl]amino]methyl]-7-thiabicyclo[2.2.1]hept-2-yl]-5-heptenoic acid, methyl ester Example 1, Part V chiral amine (1.5 mmol) is dissolved in distilled THF (20 ml) in an argon atmosphere. Part B acid (1.55 mmol) is added and the mixture is cooled in an ice bath. Dicyclohexylcarbodiimide (DDC) (319 mg, 1.55 mmol) is added and the mixture is stirred cold 20 minutes and at room temperature overnight. 1N HCl (4 drops) is added and after stirring 10 minutes the solvent is removed in vacuo. EtOAc (8 ml) is added to the residue. After cooling in an ice bath the solid is removed by filtration and washed with cold EtOAc (~10 ml). The filtrate is freed of solvent in vacuo and the remaining material is chromatographed on silica gel (Baker for flash chromatography) eluting with EtOAc and 3% MeOH in EtOAc to give title ester.

D. [1α,2β(Z),3β,4α]-7-[3-[[[[3-(4-Hydroxyphenyl)-1-oxopropyl]amino]acetyl]amino]methyl]-7-thiabicyclo[2.2.1]hept-2-yl]-5-heptenoic acid The Part C methyl ester (0.51 mmol) is dissolved in distilled THF (20 ml) and water (2 ml) in an argon atmosphere and treated with 1N LiOH solution (3 ml). The reaction appears complete by TLC in 1 hour and at 2 hours is worked up as described in Example 6 to form the acid product.

EXAMPLE 38

[1α,2β(Z),3β,4α]-7-[3-[[[[(Phenoxyacetyl)-amino]acetyl]amino]methyl]-7-thiabicyclo[2.2.1]hept-2-yl]-5-heptenoic acid

A. Phenoxyacetyl glycine

Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

B. [1α,2β(Z),3β,4α]-7-[3-[[[[(Phenoxyacetyl)amino]acetyl]amino]methyl]-7-thiabicyclo[2.2.1]hept-2-yl]-5-heptenoic acid, methyl ester Part A acid (1.5 mmol) is reacted with CDI (1.5 mmol), followed by Example 1 Part V chiral amine (1.5 mmol) as described in Example 5, Part B. The crude product is chromatographed on silica gel (Baker for flash chromatography) eluting with EtOAc and 2% MeOH in EtOAc to give title ester.

C. [1α,2β(Z),3β,4α]-7-[3-[[[[(Phenoxyacetyl)amino]acetyl]amino]methyl]-7-thiabicyclo[2.2.1]hept-2-yl]-5-heptenoic acid The Part B methyl ester (1.01 mmol) is hydrolyzed with 1N LiOH (2 equivalents) in a THF-H$_2$O mixture as described in Example 6 to give a white solid. This is recrystallized from EtOAc (20 ml) containing a few drops of MeOH to give title acid.

EXAMPLE 39

[1α,2β(5Z),3β,4α]-7-[3-[[[[(1-Oxo-3-phenylpropyl)amino]acetyl]amino]methyl]-7-thiabicyclo[2.2.1]hept-2-yl]-5-heptenoic acid

A. 3-Phenylpropanoyl glycine

Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried (MgSO$_4$) and freed of solvent in vacuo leaving a near white solid (3.53 g, 85%). This was recrystallized from EtOAc (13 ml) to give title compound (2.66 g, 64%) m.p. 112°–114° C.

B. [1α,2β(5Z),3β,4α]-7-[3-[[[[(1-Oxo-3-phenylpropyl)amino]acetyl]amino]methyl]-7-thiabicyclo[2.2.1]hept-2-yl]-5-heptenoic acid, methyl ester Part A acid (1 mmol) is reacted with CDI (1 mmol) and then with Example 1 Part V chiral amine (1 mmol) as described in Example 5 Part B. The crude product is chromatographed on silica gel (Baker for flash chromatography), eluting with 2% MeOH in EtOAc to give the title compound.

C. [1α,2β(5Z),3β,4α]-7-[3-[[[[(1-Oxo-3-phenylpropyl)amino]acetyl]amino]methyl]-7-thiabicyclo[2.2.1]hept-2-yl]-5-heptenoic acid The Part B methyl ester (0.72 mmol) is hydrolyzed with LiOH in a water-THF mixture as described in Example 6. The crude crystalline product is recrystallized from EtOAc (12 ml) to give title compound.

EXAMPLE 40

[1α,2β(5Z),3β,4α]-7-[3-[[[[(1-Oxo-5-phenylpentyl)amino]acetyl]amino]methyl]-7-thiabicyclo[2.2.1]hept-2-yl]-5-heptenoic acid

A. 5-Phenylpentanoyl glycine ethyl ester

5-Phenylvaleric acid (2.67 g, 15 mmol) in distilled THF was reacted with CDI (15 mmol) followed by glycine ethyl ester.HCl (15 mmol) and (C$_2$H$_5$)$_3$N (15 mmol) as described in Example 35 Part A. The crude material (3.25 g, 82%) was used without purification.

B. 5-Phenylpentanoyl glycine

The Part A ester (12.34 mmol) was hydrolyzed with NaOH in water as described in Example 56 Part B. The crude product was recrystallized from EtOAc (12 ml) to give title compound (2.39 g, 82%), m.p. 93°–96° C.

C. [1α,2β(5Z),3β,4α]-7-[3-[[[[(1-Oxo-5-phenylpentyl)amino]acetyl]amino]methyl]-7-thiabicyclo[2.2.1]hept-2-yl]-5-heptenoic acid, methyl ester Part B compound (1 mmol) is reacted with CDI (1 mmol) and then with Example 1 Part V chiral amine (1 mmol) as described in Example 5 Part B. The crude product is chromatographed on silica gel (Baker for flash chromatography) eluting with 2% MeOH in EtOAc to give title compound.

D. [1α,2β(5Z),3β,4α]-7-[3-[[[[(1-Oxo-5-phenylpentyl)amino]acetyl]amino]methyl]-7-thiabicyclo[2.2.1]-hept-2-yl]-5-heptenoic acid The Part C methyl ester (0.749 mmol) is hydrolyzed with LiOH in a water-THF mixture as described in Example 6. The crude crystalline product is recrystallized from EtOAc (10 ml) containing a few drops of MeOH to give title compound.

EXAMPLE 41

[1α,2β(Z),3β,4α]-7-[3-[[[[(4-Cyclohexyl-1-oxobutyl)amino]acetyl]amino]methyl]-7-thiabicyclo[2.2.1]hept-2-yl]-5-heptenoic acid

A. 4-Cyclohexylbutanoic acid

4-Phenylbutanoic acid prepared as described in Example 56, Part A was dissolved in glacial acetic acid (25 ml). Platinum oxide (0.1 g) was added and the solution was hydrogenated in the Paar shaker at up to 55 p.s.i. until hydrogen uptake ceased (6.5 hours). The catalyst was removed by filtration and the acetic acid was removed in vacuo. The product crystallized and was recrystallized from Et$_2$O (20 ml) to give title compound (1.18 g, 77%), m.p. 85°–88° C.

B. [1α,2β(Z),3β,4α]-7-[3-[[[[(4-Cyclohexyl-1-oxobutyl)amino]acetyl]amino]methyl]-7-thiabicyclo[2.2.1]hept-2-yl]-5-heptenoic acid, methyl ester The Part A acid (1.5 mmol) is dissolved in CHCl$_3$ (10 ml) in an argon atmosphere. The solution is cooled in an ice bath and carbonyldiimidazole (2.43 mg, 1.5 mmol) is added. The mixture is stirred cold 30 minutes and at room temperature 1 hour. The hydrochloride of the chiral amine (prepared as described in Example 1 Part V) (1.5 mmol) is added. The solution is cooled in an ice bath and tri-n-butylamine (0.36 ml, 278 mg, 1.5 mmol) is added and the mixture is left stirring overnight at room temperature. More CHCl$_3$ (40 ml) is added and the solution is washed with 1N HCl (20 ml), saturated NaHCO$_3$ solution (20 ml) and saturated NaCl solution (20 ml). After drying (MgSO$_4$), the solvent is removed in vacuo. The product is purified by chromatography on silica gel (Baker for flash chromatography) eluting with 1% MeOH in EtOAc to give the title methyl ester.

C.

[1α,2β(Z),3β,4α]-7-[3-[[[[(4-Cyclohexyl-1-oxobutyl)amino]acetyl]amino]methyl]-7-thiabicyclo[2.2.1]hept-2-yl]-5-heptenoic acid The Part B methyl ester (1.39 mmol) is hydrolyzed with LiOH as described in Example 6. The crude crystalline product is recrystallized from EtOAc (15 ml) and MeOH (1 ml) to give title acid compound.

EXAMPLE 42

[1α,2β(Z),3β,4α]-7-[3-[[[[1-Oxo-3-(phenylthio)propyl]amino]acetyl]amino]methyl]-7-thiabicyclo[2.2.1]hept-2-yl]-5-heptenoic acid

A. 3-(Phenylthio)propanoic acid, methyl ester

Thiophenol (440 mg, 4 mmol) and Et$_3$N (70 μl, 0.5 mmol) were dissolved in CH$_2$Cl$_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, Et$_2$O-hexane 1:2, UV R$_f$=0.58. The crude title ester was used without further purification.

B. 3-(Phenylthio)propanoic acid

The crude Part A methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with Et$_2$O (20 ml) and then acidified with concentrated HCl. The product was extracted with CHCl$_3$ (2×30 ml). The chloroform extracts were washed with saturated NaCl solution (2×20 ml), dried (MgSO$_4$) and freed of solvent in vacuo leaving title acid as a white solid (quant.). This was used without further purification.

C. 3-(Phenylthio)propanoyl glycine ethyl ester

Part B acid (0.740 g, 4.06 mmol) was reacted with carbonyldiimidazole (4.06 mmol) followed by glycine ethyl ester.HCl (4.06 mmol) as described in Example 56 Part A to give the title ester (1.00 g, 92%) as crystalline material.

D. 3-(Phenylthio)propanoyl glycine

The Part C ethyl ester (0.96 g, 3.6 mmol) was hydrolyzed with NaOH solution as described in Example 56 Part B to give a white solid which was triturated with Et$_2$O to give title acid (0.75 g, 87%).

E.

[1α,2β(Z),3β,4α]-7-[3-[[[[1-Oxo-3-(phenylthio)propyl]amino]acetyl]amino]methyl]-7-thiabicyclo[2.2.1]hept-2-yl]-5-heptenoic acid, methyl ester The Part D acid (1.5 mmol) is reacted with carbonyldiimidazole (1.5 mmol) followed by the hydrochloride of Example 1 Part V chiral amine by the procedure described in Example 62 Part B. The crude product is chromatographed on silica gel (Baker for flash chromatography), eluting with 1% MeOH in EtOAc to give the title methyl ester.

F.

[1α,2β(Z),3β,4α]-7-[3-[[[[1-Oxo-3-(phenylthio)propyl]amino]acetyl]amino]methyl]-7-thiabicyclo[2.2.1]hept-2-yl]-5-heptenoic acid The Part E methyl ester (1.285 mmol) is dissolved in THF (25 ml) and H$_2$O (2.5 ml) in an argon atmosphere and treated with 1N LiOH solution (2.6 ml). The mixture is stirred at room temperature for 5 hours and then worked up as described in Example 6. The crude product is chromatographed on silica gel (Baker for flash chromatography) eluting with 5% MeOH in CH$_2$Cl$_2$ to give title acid.

EXAMPLE 43

[1α,2β(Z),3β,4α]-7-[3-[[[[[(Phenylmethyl)thio]acetyl]amino]acetyl]amino]methyl]-7-thiabicyclo[2.2.1]hept-2-yl]-5-heptenoic acid

A. Chloroacetyl glycine

Glycine (1.5 g, 20 mmol) was dissolved in 2N NaOH (25 ml, 50 mmol) and ether (20 ml) was added. Chloroacetyl chloride (2.26 g) dissolved in Et$_2$O (20 ml) was added dropwise at 0° C. The mixture was stirred at 0° for 30 minutes and at room temperature 1 hour. The layers were separated and the water layer was washed with Et$_2$O (2×20 ml). The water layer was then acidified to pH 2 with concentrated HCl and the product was extracted into EtOAc (3×50 ml). The combined EtOAc extracts were washed with brine, dried (MgSO$_4$), and freed of solvent in vacuo to give title acid compound as a solid (2.56 g, 84%) which was used without further purification.

B. (Benzylthio)acetyl glycine

Part A acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with Et$_2$O (3×50 ml), washed with brine, dried (MgSO$_4$) and freed of solvent in vacuo leaving a white solid. This was recrystallized from benzene to give title acid compound (1.28 g, 64%).

C.

[1α,2β(Z),3β,4α]-7-[3-[[[[[(Phenylmethyl)thio]acetyl]amino]acetyl]amino]methyl]-7-thiabicyclo[2.2.1]hept-2-yl]-5-heptenoic acid, methyl ester Part B acid (1.5 mmol) is reacted with carbonyldiimidazole (1.5 mmol) followed by Example 1 Part V chiral amine.HCl 3 (1.5 mmol) using the procedure described in Example 41. The crude product is chromatographed on silica gel (Baker for flash chromatography) eluting with 1% MeOH in EtOAc to give title ester.

D.
[1α,2β(Z),3β,4α]-7-[3-[[[[[[(Phenylmethyl)thio]acetyl]amino]acetyl]amino]methyl]-7-thiabicyclo[2.2.1]hept-2-yl]-5-heptenoic acid The Part C methyl ester (1.28 mmol) is hydrolyzed with 1N LiOH solution (2.6 ml) in a THF-water mixture as described in Example 5 Part B. The reaction mixture is worked up at 5 hours and the crude product is recrystallized from EtOAc (15 ml) to give title product.

EXAMPLE 44

[1α,2β(Z),3β,4α]-7-[3-[[[[[(Butylthio)acetyl]amino]acetyl]amino]methyl]-7-thiabicyclo[2.2.1]hept-2-yl]-5-heptenoic acid

A. (Butanethio)acetyl glycine

Example 43 Part A acid compound (8.4 mmol) is reacted with 1-butanethiol using the procedure described in Example 43. The crude product is crystallized with diisopropylether (~10 ml) to give title acid.

B.
[1α,2β(Z),3β,4α]-7-[3-[[[[[(Butylthio)acetyl]amino]acetyl]amino]methyl]-7-thiabicyclo[2.2.1]hept-2-yl]-5-heptenoic acid, methyl ester Part A acid (1.5 mmol) is reacted with carbonyldiimidazole (1.5 mmol) followed by Example 1 Part V chiral amine hydrochloride (1.5 mmol) using the procedure described in Example 41. The crude product is chromatographed on silica gel (Baker for flash chromatography) eluting with 1% MeOH in EtOAc to give title compound.

C.
[1α,2β(Z),3β,4α]-7-[3-[[[[[(Butylthio)acetyl]amino]acetyl]amino]methyl]-7-thiabicyclo[2.2.1]hept-2-yl]-5-heptenoic acid The Part B methyl ester (1.18 mmol) is hydrolyzed with 1N LiOH solution (2.4 ml) in a tetrahydrofuran-water mixture using the procedure described in Example 5 Part B. The reaction mixture is worked up in 5 hours. The crude product is crystallized from EtOAC (20 ml) to give title product.

EXAMPLE 45

[1α,2β(Z),3β,4α]-7-[3-[[[[[(Cyclohexylmethyl)-thio]acetyl]amino]acetyl]amino]methyl]-7-thiabicyclo[2.2.1]hept-2-yl]-5-heptenoic acid

A. Cyclohexymethylthiol acetate

Cyclohexylmethyl mesylate (1.92 g, 10 mol) and KSCOCH$_3$ (1.25 g) were suspended in distilled tetrahydrofuran (THF). The reaction mixture was heated under reflux for 3 hours. Additional KSCOCH$_3$ (1.25 g) and THF (9 ml) were added and the mixture was heated under reflux an additional 3 hours. Et$_2$O (100 ml) was added and the mixture was washed with brine (30 ml). The aqueous layer was reextracted with Et$_2$O (30 ml). The combined organic layers were washed with brine (15 ml), dried (MgSO$_4$) and freed of solvent to give a straw colored oil (1.8 g). This was chromatographed on silica gel (50 g, Baker for flash chromatography) eluting with 2% Et$_2$O in hexane to give title compound (1.189 g, 69%) as an oil. TLC: silica gel, 10% Et$_2$O in hexane, UV and I$_2$, R$_f$=0.48.

B. [(Cyclohexylmethyl)thio]acetyl glycine

Part A compound (6 mmol) and the Example 43 Part A acid (6 mmol) were reacted in the presence of NaOMe (17 mmol) as described in Example 43 Part B. The crude product was crystallized from diisopropyl ether to give title compound (516 mg, 35%).

C.
[1α,2β(Z),3β,4α]-7-[3-[[[[[(Cyclohexylmethyl)thio]acetyl]amino]acetyl]amino]methyl]-7-thiabicyclo[2.2.1]hept-2-yl]-5-heptenoic acid, methyl ester Part B compound (1.5 mmol) is coupled with Example 1 Part V chiral amine.HCl (1.5 mmol) in the presence of carbonyl diimidazole (CDI) (1.5 mmol) as described in Example 41 Part B. The crude product is chromatographed on silica gel (30 g, Baker for flash chromatography) eluting with 1% MeOH in EtOAc to give title compound.

D.
[1α,2β(Z),3β,4α]-7-[3-[[[[[(Cyclohexylmethyl)thio]acetyl]amino]acetyl]amino]methyl]-7-thiabicyclo[2.2.1]hept-2-yl]-5-heptenoic acid The Part C methyl ester (1.09 mmol) is hydrolyzed with 1N LiOH (4 ml) in a mixture of THF and water as described in Example 6. The crude product is recrystallized from EtOAc (30 ml) to give title acid.

EXAMPLE 46

[1α,2β(Z),3β,4α]-7-[3-[[[[[(Phenylsulfinyl)-acetyl]amino]acetyl]amino]methyl]-7-thiabicyclo[2.2.1]hept-2-yl]-5-heptenoic acid Powdered NaIO$_4$ (385 mg, 1.8 mmol) is dissolved in water (12 ml). A solution of Example 36 acid compound (0.6 mmol) in methanol (20 ml) is added. The mixture is stirred overnight at room temperature. Most of the methanol is removed in vacuo. Saturated NaCl solution (50 ml) is added. The product is extracted with CHCl$_3$ (3×50 ml). The combined chloroform extracts are washed with NaCl solution (20 ml), dried (MgSO$_4$), and freed of solvent in vacuo leaving an oil. This is chromatographed on silica gel (Baker for flash chromatography) eluting with 5% MeOH in CH$_2$Cl$_2$ to give title acid.

EXAMPLE 47

[1α,2β(Z),3β,4α]-7-[3-[[[[[(Phenylsulfonyl)acetyl]amino]acetyl]amino]methyl]-7-thiabicyclo[2.2.1]hept-2-yl]-5-heptenoic acid Example 36 acid compound (0.9 mmol) is dissolved in methanol (10 ml) and cooled in an ice bath. Oxone (810 mg ~2.7 mmol) dissolved in water (10 ml) is added. The mixture is stirred at room temperature 4 hours, then diluted with water (30 ml). The product is extracted into CHCl$_3$ (3×35 ml). The combined CHCl$_3$ extracts are washed with saturated NaCl solution (2×20 ml), dried (MgSO$_4$), and freed of solvent in vacuo leaving an oil. This is chromatographed on silica gel (Baker for flash chromatography) eluting with 5% MeOH in CH$_2$Cl$_2$ to give title acid.

EXAMPLES 48 TO 75

Following the procedures outlined in the specification and described in the above working examples, the following compounds may be prepared.

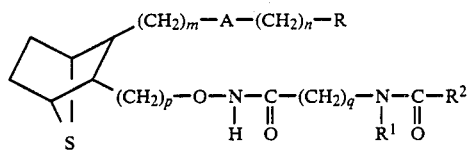

| Ex. No. | m | A | $(CH_2)_n$ | R | p | $(CH_2)_q$ | $R^1$ | $R^2$ |
|---|---|---|---|---|---|---|---|---|
| 48. | 2 | CH=CH | $CH_2$ | $CO_2H$ | 1 | $(CH_2)_2$ | $CH_3$ | H |
| 49. | 3 | $(CH_2)_2$ | $(CH_2)_2$ | $CH_2OH$ | 2 | $(CH_2)_3$ | H | $CH_3$ |
| 50. | 4 | CH=CH | $(CH_2)_3$ | tetrazole-CH< | 3 | $(CH_2)_4$ | H | $-CH=CH-CH_3$ |
| 51. | 1 | $(CH_2)_2$ | $(CH_2)_4$ | $-C(O)N(CH_3)C_2H_5$ | 1 | $(CH_2)_5$ | $CH_3$ | $-C\equiv C-CH_3$ |
| 52. | 1 | CH=CH | $(CH_2)_5$ | $-C(O)N(CH_3)-OH$ | 2 | $(CH_2)_6$ | $C_2H_5$ | $-CH_2-C\equiv C-CH_3$ |
| 53. | 2 | CH=CH | $-CH(CH_3)-$ | $-C(O)N(H)-OCH_3$ | 3 | $(CH_2)_7$ | $C_3H_7$ | $-CH_2-CH=CH-CH_3-$ |
| 54. | 3 | $(CH_2)_2$ | $-C(CH_3)_2-$ | $-C(O)N(CH_3)-OC_2H_5$ | 4 | $-CH(CH_3)-$ | $C_4H_9$ | $C_6H_5$ |
| 55. | 4 | $(CH_2)_2$ | $(CH_2)_4$ | $-C(O)NHC_6H_5$ | 1 | $-CH_2-$ | $C_5H_{11}$ | $C_6H_5S$ |
| 56. | 1 | CH=CH | $-C(CH_3)_2-CH_2-$ | $CO_2Li$ | 2 | $-CH_2-CH(CH_3)-$ | H | $CH_2C_6H_5$ |
| 57. | 1 | CH=CH | $-CH(CH_3)-CH(CH_3)-$ | $CO_2Na$ | 3 | $-CH_2-C(CH_3)_2-$ | H | $-(CH_2)_2C_6H_5$ |
| 58. | 1 | $(CH_2)_2$ | $-C(CH_3)(F)-CH_2-$ | $CO_2$ glucamine salt | 4 | $-CH_2-CH(CH_3)-CH_2-$ | H | $-C_6H_4-p-CH_3$ |
| 59. | 2 | CH=CH | $-CH(F)-CH(F)-$ | $CO_2$ tris salt | 1 | $-(CH_2)_3-$ | $CH_3$ | $-C_6H_4-p-OH$ |
| 60. | 3 | $(CH_2)_2$ | $-C(F)_2-CH_2-$ | $CH_2OH$ | 2 | $-CH_2-CH(C_2H_5)(CH_3)$ | $CH_3$ | $-OCH_3$ |
| 61. | 4 | $(CH_2)_2$ | $-(CH_2)_5$ | tetrazole-CH< | 3 | $-CH_2-CH-CH_2-$ | $CH_3$ | $-C_2H_5S$ |
| 62. | 1 | CH=CH | $-CH_2-CH(CH_3)-CH_2-$ | $-C(O)NH_2$ | 4 | $-C(CH_3)_2-CH_2-$ | $C_2H_5$ | $-OC_6H_5$ |

-continued

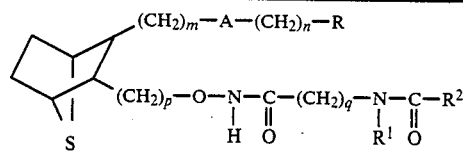

| Ex. No. | m | A | $(CH_2)_n$ | R | p | $(CH_2)_q$ | $R^1$ | $R^2$ |
|---|---|---|---|---|---|---|---|---|
| 63. | 1 | $(CH_2)_2$ | $-CH_2-\underset{\underset{CH_3}{\|}}{\overset{\overset{CH_3}{\|}}{C}}-$ | $\underset{H}{\overset{O}{\underset{\|}{C}}}NOH$ | 1 | $(CH_2)_2$ | $CH_3$ | $-NH_2$ |
| 64. | 1 | CH=CH | $CH_2$ | $\overset{O}{\underset{\|}{C}}N(CH_3)_2$ | 2 | $-CH_2-$ | H | $-NHCH_3$ |
| 65. | 2 | $(CH_2)_2$ | $(CH_2)_2$ | $\overset{O}{\underset{\|}{C}}N\underset{OH}{-CH_3}$ | 3 | $-CH_2-\underset{\underset{CH_3}{\|}}{\overset{\overset{CH_3}{\|}}{C}}-$ | $C_4H_9$ | $-NHC_6H_5$ |
| 66. | 3 | CH=CH | $(CH_2)_3$ | $CO_2H$ | 4 | $-CH_2-\overset{CH_3}{\underset{\|}{CH}}-\overset{CH_3}{\underset{\|}{CH}}-CH_2-$ | $CH_3$ | $NCH_3(C_2H_5)$ |
| 67. | 4 | $(CH_2)_2$ | $(CH_2)_4$ | $CH_2OH$ | 1 | $(CH_2)_2$ | $C_2H_5$ | $-N(CH_3)_2$ |
| 68. | 1 | CH=CH | $-CH_2\overset{F}{\underset{F}{C}}-$ | triazole | 2 | $(CH_2)_3$ | $CH_3$ | H |
| 69. | 1 | $(CH_2)_2$ | $-CH_2-\underset{\underset{CH_3}{\|}}{\overset{\overset{CH_3}{\|}}{C}}-$ | $\overset{O}{\underset{\|}{C}}N(C_2H_5)_2$ | 3 | $-\overset{F}{\underset{\|}{CH}}-CH_2-$ | $C_3H_7$ | $C_4H_9$ |
| 70. | 2 | CH=CH | $(CH_2)_5$ | $\overset{O}{\underset{\|}{C}}NHC_6H_5$ | 4 | $-\overset{F}{\underset{F}{C}}-CH_2$ | $CH_4H_9$ | $-(CH_2)_2CH=CHCH_3$ |
| 71. | 3 | $(CH_2)_2$ | $-CH_2-\overset{CH_3}{\underset{\|}{CH}}-\overset{F}{\underset{\|}{}}$ | $CH_2OH$ | 1 | $(CH_2)_2$ | H | $-\overset{O}{\underset{\|}{S}}C_6H_5$ |
| 72. | 4 | $(CH_2)_2$ | $(CH_2)_2$ | triazole | 2 | $CH_2$ | H | $-\overset{O}{\underset{\underset{O}{\|}}{\overset{\|}{S}}}-CH_2C_6H_5$ |
| 73. | 1 | CH=CH | $(CH_2)_3$ | $CO_2CH_3$ | 3 | $(CH_2)_3$ | $C_3H_7$ | $-OC_4H_9$ |
| 74. | 2 | $(CH_2)_2$ | $(CH_2)_4$ | $CO_2CH_3$ | 4 | $(CH_2)_8$ | H | $-OC_6H_5$ |
| 75. | 3 | CH=CH | $(CH_2)_5$ | $CO_2H$ | 1 | $(CH_2)_{10}$ | H | $-S-CH_2C_6H_5$ |

EXAMPLES 76 TO 103

Following the procedures outlined in the specification and described in the above working examples, the following compounds may be prepared.

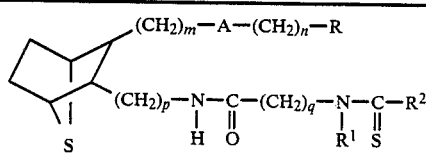

| Ex. No. | m | A | $(CH_2)_n$ | R | p | $(CH_2)_q$ | $R^1$ | $R^2$ |
|---|---|---|---|---|---|---|---|---|
| 76. | 2 | CH=CH | $CH_2$ | $CO_2H$ | 1 | $(CH_2)_2$ | $CH_3$ | H |
| 77. | 3 | $(CH_2)_2$ | $(CH_2)_2$ | $CH_2OH$ | 2 | $(CH_2)_3$ | H | $CH_3$ |

-continued

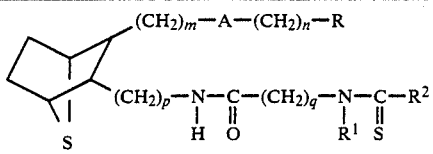

| Ex. No. | m | A | (CH$_2$)$_n$ | R | p | (CH$_2$)$_q$ | R$^1$ | R$^2$ |
|---|---|---|---|---|---|---|---|---|
| 78. | 4 | CH=CH | (CH$_2$)$_3$ | tetrazole (N—N / N—N—H with CH$_3$) | 3 | (CH$_2$)$_4$ | H | —CH$_2$—CH=CH—CH$_3$ |
| 79. | 1 | (CH$_2$)$_2$ | (CH$_2$)$_4$ | $\overset{O}{\overset{\|}{C}}$N(CH$_3$)C$_2$H$_5$ | 1 | (CH$_2$)$_5$ | CH$_3$ | —C≡C—CH$_3$ |
| 80. | 1 | CH=CH | (CH$_2$)$_5$ | $\overset{O}{\overset{\|}{C}}$N(CH$_3$)—OH | 2 | (CH$_2$)$_6$ | C$_2$H$_5$ | —CH$_2$—CH$_2$—C≡CH |
| 81. | 2 | CH=CH | —CH(CH$_3$)— | $\overset{O}{\overset{\|}{C}}$N(H)—OCH$_3$ | 3 | C$_2$H$_5$ | C$_3$H$_7$ | —CH$_2$—CH=CH—CH$_3$ |
| 82. | 3 | (CH$_2$)$_2$ | —C(CH$_3$)$_2$— | $\overset{O}{\overset{\|}{C}}$N(CH$_3$)—OC$_2$H$_5$ | 4 | —CH(CH$_3$)— | C$_4$H$_9$ | C$_6$H$_5$S |
| 83. | 4 | (CH$_2$)$_2$ | (CH$_2$)$_4$ | $\overset{O}{\overset{\|}{C}}$NHC$_6$H$_5$ | 1 | —CH$_2$— | C$_5$H$_{11}$ | C$_6$H$_5$ |
| 84. | 1 | CH=CH | —C(CH$_3$)$_2$—CH$_2$— | CO$_2$Li | 2 | —CH$_2$—CH(CH$_3$)— | H | CH$_2$C$_6$H$_5$ |
| 85. | 1 | CH=CH | —CH(CH$_3$)—CH(CH$_3$)— | CO$_2$Na | 3 | —CH$_2$—C(CH$_3$)$_2$— | H | —(CH$_2$)$_2$C$_6$H$_5$ |
| 86. | 1 | (CH$_2$)$_2$ | —C(CH$_3$)(F)—CH$_2$— | CO$_2$glucamine salt | 4 | —CH$_2$—CH(CH$_3$)—CH$_2$— | H | —C$_6$H$_4$—p-CH$_3$ |
| 87. | 2 | CH=CH | —CH(F)—CH(F)— | CO$_2$tris salt | 1 | —(CH$_2$)$_3$— | CH$_3$ | —C$_6$H$_4$—p-OH |
| 88. | 3 | (CH$_2$)$_2$ | —C(F)$_2$—CH$_2$— | CH$_2$OH | 2 | —CH$_2$—CH(C$_2$H$_5$)— | CH$_3$ | —OCH$_3$ |
| 89. | 4 | (CH$_2$)$_2$ | —(CH$_2$)$_5$— | tetrazole (N—N / N—N—H with CH$_3$) | 3 | —CH$_2$—C(CH$_3$)(H)—CH$_2$— | CH$_3$ | —OC$_2$H$_5$ |
| 90. | 1 | CH=CH | —CH$_2$—CH(CH$_3$)—CH$_2$— | $\overset{O}{\overset{\|}{C}}$NH$_2$ | 4 | —C(CH$_3$)$_2$—CH$_2$— | C$_2$H$_5$ | —OCH$_2$C$_6$H$_5$ |
| 91. | 1 | (CH$_2$)$_2$ | —CH$_2$—C(CH$_3$)$_2$— | $\overset{O}{\overset{\|}{C}}$N(H)OH | 1 | (CH$_2$)$_2$ | CH$_3$ | —NH$_2$ |
| 92. | 1 | CH=CH | CH$_2$ | $\overset{O}{\overset{\|}{C}}$N(CH$_3$)$_2$ | 2 | —CH$_2$— | H | —NHCH$_3$ |

-continued

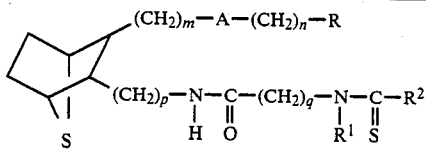

| Ex. No. | m | A | $(CH_2)_n$ | R | p | $(CH_2)_q$ | $R^1$ | $R^2$ |
|---|---|---|---|---|---|---|---|---|
| 93. | 2 | $(CH_2)_2$ | $(CH_2)_2$ | $\underset{OH}{\overset{O}{\underset{\|}{C}}}N-CH_3$ | 3 | $-CH_2-\underset{CH_3}{\overset{CH_3}{\underset{\|}{C}}}-$ | $C_4H_9$ | $-NHC_6H_5$ |
| 94. | 3 | CH=CH | $(CH_2)_3$ | $CO_2H$ | 4 | $-CH_2-\overset{CH_3}{\underset{\|}{CH}}-\overset{CH_3}{\underset{\|}{CH}}-CH_2-$ | $CH_3$ | $NCH_3(C_2H_5)$ |
| 95. | 4 | $(CH_2)_2$ | $(CH_2)_4$ | $CH_2OH$ | 1 | $(CH_2)_2$ | $C_2H_5$ | $-N(CH_3)_2$ |
| 96. | 1 | CH=CH | $-CH_2\overset{F}{\underset{F}{C}}-$ | tetrazolyl | 2 | $(CH_2)_3$ | $CH_3$ | H |
| 97. | 1 | $(CH_2)_2$ | $-CH_2-\overset{CH_3}{\underset{CH_3}{C}}-$ | $\overset{O}{\underset{\|}{C}}N(C_2H_5)_2$ | 3 | $-\overset{F}{\underset{\|}{CH}}-CH_2-$ | $C_3H_7$ | $C_4H_9S$ |
| 98. | 2 | CH=CH | $(CH_2)_5$ | $\overset{O}{\underset{\|}{C}}NHC_6H_5$ | 4 | $-\overset{F}{\underset{F}{C}}-CH_2$ | $CH_4H_9$ | $-(CH_2)_2CH=CHCH_3$ |
| 99. | 3 | $(CH_2)_2$ | $-CH_2-\overset{CH_3}{\underset{\|}{CH}}\overset{F}{\underset{\|}{}}-$ | $CH_2OH$ | 1 | $(CH_2)_2$ | H | $\overset{O}{\underset{O}{\overset{\|}{S}}}-C_6H_5$ |
| 100. | 4 | $(CH_2)_2$ | $(CH_2)_2$ | $CH_2OH$-tetrazolyl | 2 | $CH_2$ | H | $-CH_2C_6H_5$ |
| 101. | 1 | CH=CH | $(CH_2)_3$ | $CO_2CH_3$ | 3 | $(CH_2)_3$ | $C_3H_7$ | $\overset{O}{\underset{\|}{-SC_4H_9}}$ |
| 102. | 2 | $(CH_2)_2$ | $(CH_2)_4$ | $CO_2CH_3$ | 4 | $(CH_2)_8$ | H | $-O(CH_2)_2C_6H_5$ |
| 103. | 3 | CH=CH | $(CH_2)_5$ | $CO_2H$ | 1 | $(CH_2)_{10}$ | H | $-NCH_3(C_6H_5)$ |

EXAMPLES 104 TO 131

Following the procedures outlined in the specification and described in the above working examples, the following compounds may be prepared.

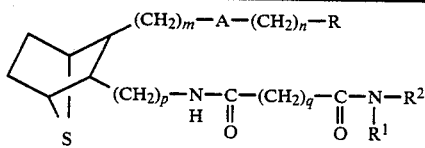

| Ex. No. | m | A | $(CH_2)_n$ | R | p | $(CH_2)_q$ | $R^1$ | $R^2$ |
|---|---|---|---|---|---|---|---|---|
| 104. | 2 | CH=CH | $CH_2$ | $CO_2H$ | 1 | $(CH_2)_2$ | $CH_3$ | H |
| 105. | 3 | $(CH_2)_2$ | $(CH_2)_2$ | $CH_2OH$ | 2 | $(CH_2)_3$ | H | $CH_3$ |

-continued

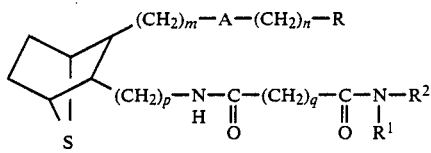

| Ex. No. | m | A | $(CH_2)_n$ | R | p | $(CH_2)_q$ | $R^1$ | $R^2$ |
|---|---|---|---|---|---|---|---|---|
| 106. | 4 | CH=CH | $(CH_2)_3$ | tetrazole (N—N / N—N—H) | 3 | $(CH_2)_4$ | H | $-CH_2CH=CH-CH_3$ |
| 107. | 1 | $(CH_2)_2$ | $(CH_2)_4$ | $-\overset{O}{\overset{\|}{C}}N(CH_3)C_2H_5$ | 1 | $(CH_2)_5$ | $CH_3$ | $-CH_2-C\equiv C-CH_3$ |
| 108. | 1 | CH=CH | $(CH_2)_5$ | $-\overset{O}{\overset{\|}{C}}\underset{CH_3}{N}-OH$ | 2 | $(CH_2)_6$ | $C_2H_5$ | $-CH_2-CH_2-C\equiv C-CH_3$ |
| 109. | 2 | CH=CH | $-\overset{CH_3}{\underset{H}{CH}}-$ | $-\overset{O}{\overset{\|}{C}}\underset{CH_3}{N}-OCH_3$ | 3 | $(CH_2)_7$ | $C_3H_7$ | $-CH_2-CH_2-\overset{H}{C}=\overset{H}{C}-CH_3$ |
| 110. | 3 | $(CH_2)_2$ | $-\overset{CH_3}{\underset{CH_3}{C}}-$ | $-\overset{O}{\overset{\|}{C}}\underset{CH_3}{N}-OC_2H_5$ | 4 | $-\overset{CH_3}{\underset{}{CH}}-$ | $C_4H_9$ | $-SC_6H_5$ |
| 111. | 4 | $(CH_2)_2$ | $(CH_2)_4$ | $-\overset{O}{\overset{\|}{C}}NHC_6H_5$ | 1 | $-CH_2-$ | $C_5H_{11}$ | $-C_6H_5$ |
| 112. | 1 | CH=CH | $-\overset{CH_3}{\underset{}{C}}\overset{CH_3}{\underset{}{-}}CH_2-$ | $CO_2Li$ | 2 | $-CH_2-\overset{CH_3}{\underset{}{CH}}-$ | H | $CH_2C_6H_5$ |
| 113. | 1 | CH=CH | $-\overset{CH_3}{\underset{}{CH}}-\overset{CH_3}{\underset{}{CH}}-$ | $CO_2Na$ | 3 | $-CH_2-\overset{CH_3}{\underset{}{C}}\overset{CH_3}{\underset{}{-}}$ | H | $-(CH_2)_2C_6H_5$ |
| 114. | 1 | $(CH_2)_2$ | $-\overset{CH_3}{\underset{F}{C}}-CH_2-$ | $CO_2$glucamine salt | 4 | $-CH_2-\overset{CH_3}{\underset{}{CH}}-CH_2-$ | H | $-C_6H_4-p-CH_3$ |
| 115. | 2 | CH=CH | $-\overset{F}{\underset{}{CH}}-\overset{F}{\underset{}{CH}}-$ | $CO_2$tris salt | 1 | $-(CH_2)_3-$ | $CH_3$ | $-C_6H_4-p-OH$ |
| 116. | 3 | $(CH_2)_2$ | $-\overset{F}{\underset{}{C}}\overset{F}{\underset{}{-}}CH_2-$ | $CH_2OH$ | 2 | $-CH_2-\overset{C_2H_5}{\underset{}{CH}}-$ | $CH_3$ | $-OCH_3$ |
| 117. | 4 | $(CH_2)_2$ | $-(CH_2)_5$ | tetrazole (N—N / N—N—H) | 3 | $-CH_2-\overset{CH_3}{\underset{H}{C}}-CH_2-$ | $CH_3$ | $-\overset{}{\underset{O}{S}}C_2H_5$ |
| 118. | 1 | CH=CH | $-CH_2-\overset{CH_3}{\underset{}{CH}}-CH_2-$ | $\overset{O}{\overset{\|}{C}}NH_2$ | 4 | $-\overset{CH_3}{\underset{CH_3}{C}}-CH_2-$ | $C_2H_5$ | $-OCH_2C_6H_5$ |
| 119. | 1 | $(CH_2)_2$ | $-CH_2-\overset{CH_3}{\underset{}{C}}\overset{CH_3}{\underset{}{-}}$ | $-\overset{O}{\overset{\|}{C}}\underset{H}{N}OH$ | 1 | $(CH_2)_2$ | $CH_3$ | cyclopentyl |

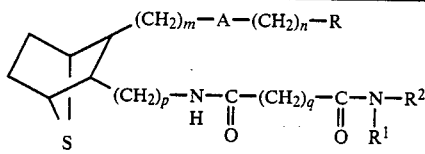

| Ex. No. | m | A | (CH₂)ₙ | R | p | (CH₂)q | R¹ | R² |
|---|---|---|---|---|---|---|---|---|
| 120. | 1 | CH=CH | CH₂ | $\underset{CN(CH_3)_2}{\overset{O}{\|}}$ | 2 | —CH₂— | H | cyclohexyl |
| 121. | 2 | (CH₂)₂ | (CH₂)₂ | $\underset{\underset{OH}{\|}}{\overset{O}{\underset{\|}{C}}}N-CH_3$ | 3 | —CH₂—C(CH₃)₂—CH₂— | C₄H₉ | —CH₂—cyclohexyl |
| 122. | 3 | CH=CH | (CH₂)₃ | CO₂H | 4 | —CH₂—CH(CH₃)—CH(CH₃)—CH₂— | CH₃ | —OCH₂—phenyl |
| 123. | 4 | (CH₂)₂ | (CH₂)₄ | CH₂OH | 1 | (CH₂)₂ | C₂H₅ | —C₇H₁₅ |
| 124. | 1 | CH=CH | —CH₂CF₂— | tetrazolyl (N-N=N-NH with CH₃) | 2 | (CH₂)₃ | CH₃ | H |
| 125. | 1 | (CH₂)₂ | —CH₂—C(CH₃)₂— | $\overset{O}{\underset{\|}{C}}N(C_2H_5)_2$ | 3 | —CHF—CH₂— | C₃H₇ | C₄H₉S |
| 126. | 2 | CH=CH | (CH₂)₅ | $\overset{O}{\underset{\|}{C}}NHC_6H_5$ | 4 | —CF₂—CH₂ | CH₄H₉ | —(CH₂)₂CH=CHCH₃ |
| 127. | 3 | (CH₂)₂ | —CH(CH₃)—CHF— | CH₂OH | 1 | (CH₂)₂ | H | C₆H₅S |
| 128. | 4 | (CH₂)₂ | (CH₂)₂ | tetrazolyl | 2 | CH₂ | H | —CH₂C₆H₅ |
| 129. | 1 | CH=CH | (CH₂)₃ | CO₂CH₃ | 3 | (CH₂)₃ | C₃H₇ | —OC₄H₉ |
| 130. | 2 | (CH₂)₂ | (CH₂)₄ | CO₂CH₃ | 4 | (CH₂)₈ | H | —OCH₂C₆H₅ |
| 131. | 3 | CH=CH | (CH₂)₅ | CO₂H | 1 | (CH₂)₁₀ | H | —NCH₃(C₆H₅) |

EXAMPLES 132 TO 159

Following the procedures outlined in the specification and described in the above working examples, the following compounds may be prepared.

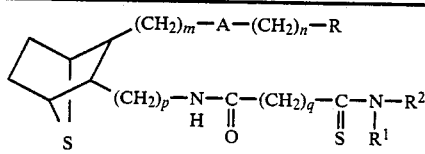

| Ex. No. | m | A | (CH₂)ₙ | R | p | (CH₂)q | R¹ | R² |
|---|---|---|---|---|---|---|---|---|
| 132. | 2 | CH=CH | CH₂ | CO₂H | 1 | (CH₂)₂ | CH₃ | H |
| 133. | 3 | (CH₂)₂ | (CH₂)₂ | CH₂OH | 2 | (CH₂)₃ | H | CH₃ |

-continued $$\text{[Structure: bicyclic with } (CH_2)_m-A-(CH_2)_n-R \text{ and } (CH_2)_p-NH-C(=O)-(CH_2)_q-C(=S)-N(R^1)R^2 \text{ substituents, with S in ring]}$$

| Ex. No. | m | A | $(CH_2)_n$ | R | p | $(CH_2)_q$ | $R^1$ | $R^2$ |
|---|---|---|---|---|---|---|---|---|
| 134. | 4 | CH=CH | $(CH_2)_3$ | tetrazole-CH | 3 | $(CH_2)_4$ | H | $-CH_2CH=CH_2$ |
| 135. | 1 | $(CH_2)_2$ | $(CH_2)_4$ | $\overset{O}{\underset{}{C}}N(CH_3)C_2H_5$ | 1 | $(CH_2)_5$ | $CH_3$ | $-CH_2C\equiv CH$ |
| 136. | 1 | CH=CH | $(CH_2)_5$ | $\overset{O}{\underset{}{C}}N(CH_3)-OH$ | 2 | $(CH_2)_6$ | $C_2H_5$ | $-CH_2-C\equiv C-CH_3$ |
| 137. | 2 | CH=CH | $-\overset{CH_3}{\underset{}{CH}}-$ | $\overset{O}{\underset{}{C}}N(H)-OCH_3$ | 3 | $(CH_2)_7$ | $C_3H_7$ | $-CH_2-\overset{H}{C}=\overset{H}{C}-CH_3-$ |
| 138. | 3 | $(CH_2)_2$ | $-\overset{CH_3}{\underset{CH_3}{C}}-$ | $\overset{O}{\underset{}{C}}N(CH_3)-OC_2H_5$ | 4 | $-\overset{CH_3}{\underset{}{CH}}-$ | $C_4H_9$ | cyclohexyl |
| 139. | 4 | $(CH_2)_2$ | $(CH_2)_4$ | $\overset{O}{\underset{}{C}}NHC_6H_5$ | 1 | $-CH_2-$ | $C_5H_{11}$ | $C_6H_5$ |
| 140. | 1 | CH=CH | $-\overset{CH_3}{\underset{}{C}}\overset{CH_3}{\underset{}{}}-CH_2-$ | $CO_2Li$ | 2 | $-CH_2-\overset{CH_3}{\underset{}{CH}}-$ | H | $CH_2C_6H_5$ |
| 141. | 1 | CH=CH | $-\overset{CH_3}{\underset{}{CH}}-\overset{CH_3}{\underset{}{CH}}-$ | $CO_2Na$ | 3 | $-CH_2-\overset{CH_3}{\underset{}{C}}\overset{CH_3}{\underset{}{}}-$ | H | $-(CH_2)_2C_6H_5$ |
| 142. | 1 | $(CH_2)_2$ | $-\overset{CH_3}{\underset{F}{C}}-CH_2-$ | $CO_2$glucamine salt | 4 | $-CH_2-\overset{CH_3}{\underset{}{CH}}-CH_2-$ | H | $-C_6H_4-p-CH_3$ |
| 143. | 2 | CH=CH | $-\overset{F}{\underset{}{CH}}-\overset{F}{\underset{}{CH}}-$ | $CO_2$tris salt | 1 | $-(CH_2)_3-$ | $CH_3$ | $-C_6H_4-p-OH$ |
| 144. | 3 | $(CH_2)_2$ | $-\overset{F}{\underset{}{C}}\overset{F}{\underset{}{}}-CH_2-$ | $CH_2OH$ | 2 | $-CH_2-\overset{C_2H_5}{\underset{}{CH}}-$ | $CH_3$ | $CH_3S-$ |
| 145. | 4 | $(CH_2)_2$ | $-(CH_2)_5-$ | tetrazole-CH | 3 | $-CH_2-\overset{CH_3}{\underset{}{CH}}-CH_2-$ | $CH_3$ | $-OC_2H_5$ |
| 146. | 1 | CH=CH | $-CH_2-\overset{CH_3}{\underset{}{CH}}-CH_2-$ | $\overset{O}{\underset{}{C}}NH_2$ | 4 | $-\overset{CH_3}{\underset{CH_3}{C}}-CH_2-$ | $C_2H_5$ | $-OCH_2C_6H_5$ |
| 147. | 1 | $(CH_2)_2$ | $-CH_2-\overset{CH_3}{\underset{}{C}}\overset{CH_3}{\underset{}{}}-$ | $\overset{O}{\underset{}{C}}N(H)OH$ | 1 | $(CH_2)_2$ | $CH_3$ | cyclopentyl |

EXAMPLES 160 TO 187

Following the procedures outlined in the specification and described in the above working examples, the following compounds may be prepared.

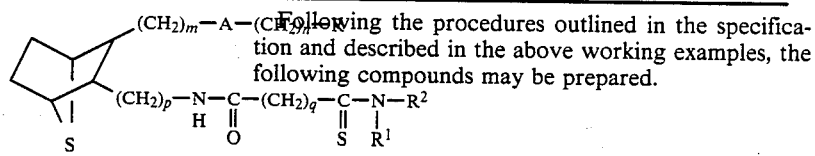

| Ex. No. | m | A | (CH₂)ₙ | R | p | (CH₂)_q | R¹ | R² |
|---|---|---|---|---|---|---|---|---|
| 148. | 1 | CH=CH | CH₂ | $\overset{O}{\overset{\|}{C}}N(CH_3)_2$ | 2 | —CH₂— | H | cyclohexyl |
| 149. | 2 | (CH₂)₂ | (CH₂)₂ | $\overset{O}{\overset{\|}{C}}N(OH)$—CH₃ | 3 | —CH₂—C(CH₃)₂—CH₃ | C₄H₉ | —CH₂—cyclohexyl |
| 150. | 3 | CH=CH | (CH₂)₃ | CO₂H | 4 | —CH₂—CH(CH₃)—CH(CH₃)—CH₂— | CH₃ | C₆H₅—CH₂—O— |
| 151. | 4 | (CH₂)₂ | (CH₂)₄ | CH₂OH | 1 | (CH₂)₂ | C₂H₅ | C₇H₁₅ |
| 152. | 1 | CH=CH | —CH₂C(F)(F)— | tetrazole | 2 | (CH₂)₃ | CH₃ | H |
| 153. | 1 | (CH₂)₂ | —CH₂—C(CH₃)₂— | $\overset{O}{\overset{\|}{C}}N(C_2H_5)_2$ | 3 | —(CH₂)₂ | C₃H₇ | C₄H₉ |
| 154. | 2 | CH=CH | (CH₂)₅ | $\overset{O}{\overset{\|}{C}}NHC_6H_5$ | 4 | —C(F)(F)—CH₂— | CH₄H₉ | —(CH₂)₂CH=CHCH₃ |
| 155. | 3 | (CH₂)₂ | —CH(CH₃)—CH(F)— | CH₂OH | 1 | (CH₂)₂ | H | C₆H₅S |
| 156. | 4 | (CH₂)₂ | (CH₂)₂ | tetrazole | 2 | CH₂ | H | —CH₂C₆H₅ |
| 157. | 1 | CH=CH | (CH₂)₃ | CO₂CH₃ | 3 | (CH₂)₃ | C₃H₇ | —OC₄H₉ |
| 158. | 2 | (CH₂)₂ | (CH₂)₄ | CO₂CH₃ | 4 | (CH₂)₈ | H | —OC₆H₅ |
| 159. | 3 | CH=CH | (CH₂)₅ | CO₂H | 1 | (CH₂)₁₀ | H | —CH₂—cyclohexyl |

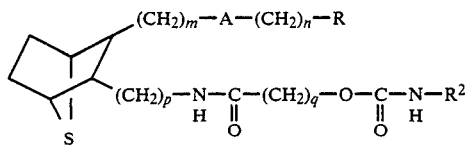

| Ex. No. | m | A | $(CH_2)_n$ | R | p | $(CH_2)_q$ | $R^2$ |
|---|---|---|---|---|---|---|---|
| 160. | 2 | CH=CH | $CH_2$ | $CO_2H$ | 1 | $(CH_2)_2$ | H |
| 161. | 3 | $(CH_2)_2$ | $(CH_2)_2$ | $CH_2OH$ | 2 | $(CH_2)_3$ | $CH_3$ |
| 162. | 4 | CH=CH | $(CH_2)_3$ | tetrazole | 3 | $(CH_2)_4$ | $-CH=CH-CH_3$ |
| 163. | 1 | $(CH_2)_2$ | $(CH_2)_4$ | $-C(O)N(CH_3)C_2H_5$ | 1 | $(CH_2)_5$ | $-C\equiv C-CH_3$ |
| 164. | 1 | CH=CH | $(CH_2)_5$ | $-C(O)N(CH_3)-OH$ | 2 | $(CH_2)_6$ | $-CH_2-C\equiv C-CH_3$ |
| 165. | 2 | CH=CH | $-CH(CH_3)-$ | $-C(O)NH-OCH_3$ | 3 | $(CH_2)_7$ | $-CH_2-CH=CH-CH_3-$ |
| 166. | 3 | $(CH_2)_2$ | $-C(CH_3)_2-$ | $-C(O)N(CH_3)-OC_2H_5$ | 4 | $-CH(CH_3)-$ | $C_6H_5S$ |
| 167. | 4 | $(CH_2)_2$ | $(CH_2)_4$ | $-C(O)NHC_6H_5$ | 1 | $-CH_2-$ | $C_6H_5S(O)$ |
| 168. | 1 | CH=CH | $-C(CH_3)_2-CH_2-$ | $CO_2Li$ | 2 | $-CH_2-CH(CH_3)-$ | $CH_2C_6H_5$ |
| 169. | 1 | CH=CH | $-CH(CH_3)-CH(CH_3)-$ | $CO_2Na$ | 3 | $-CH_2-C(CH_3)_2-$ | $-(CH_2)_2C_6H_5$ |
| 170. | 1 | $(CH_2)_2$ | $-CF(CH_3)-CH_2-$ | $CO_2$glucamine salt | 4 | $-CH_2-CH(CH_3)-CH_2-$ | $-C_6H_4-p-CH_3$ |
| 171. | 2 | CH=CH | $-CHF-CHF-$ | $CO_2$tris salt | 1 | $-(CH_2)_3-$ | $-C_6H_4-p-OH$ |
| 172. | 3 | $(CH_2)_2$ | $-CF_2-CH_2-$ | $CH_2OH$ | 2 | $-CH_2-CH(C_2H_5)-$ | $-CH_3$ |
| 173. | 4 | $(CH_2)_2$ | $-(CH_2)_5$ | tetrazole | 3 | $-CH_2-C(CH_3)(H)-CH_2-$ | $C_2H_5S$ |
| 174. | 1 | CH=CH | $-CH_2-CH(CH_3)-CH_2-$ | $-C(O)NH_2$ | 4 | $-C(CH_3)_2-CH_2-$ | $-C_6H_5$ |
| 175. | 1 | $(CH_2)_2$ | $-CH_2-C(CH_3)_2-$ | $-C(O)NHOH$ | 1 | $(CH_2)_2$ | $-(CH_2)_3-C_6H_5$ |

-continued

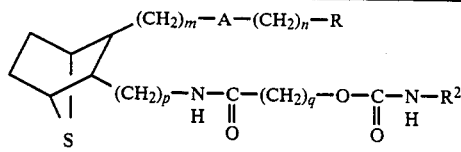

| Ex. No. | m | A | (CH₂)ₙ | R | p | (CH₂)q | R² |
|---|---|---|---|---|---|---|---|
| 176. | 1 | CH=CH | CH₂ | $\overset{O}{\underset{}{\overset{\|}{C}}}N(CH_3)_2$ | 2 | —CH₂— | C₆H₁₃ |
| 177. | 2 | (CH₂)₂ | (CH₂)₂ | $\overset{O}{\underset{OH}{\overset{\|}{C}}}N{-}CH_3$ | 3 | $-CH_2-\underset{CH_3}{\overset{CH_3}{C}}-$ | C₅H₁₁ |
| 178. | 3 | CH=CH | (CH₂)₃ | CO₂H | 4 | $-CH_2-\underset{}{\overset{CH_3}{CH}}-\underset{}{\overset{CH_3}{CH}}-CH_2-$ | —(CH₂)₂—C₆H₅ |
| 179. | 4 | (CH₂)₂ | (CH₂)₄ | CH₂OH | 1 | (CH₂)₂ | —(CH₂)₄—C₆H₅ |
| 180. | 1 | CH=CH | $-CH_2\underset{F}{\overset{F}{C}}-$ | (tetrazolyl) | 2 | (CH₂)₃ | H |
| 181. | 1 | (CH₂)₂ | $-CH_2-\underset{CH_3}{\overset{CH_3}{C}}-$ | $\overset{O}{\underset{}{\overset{\|}{C}}}N(C_2H_5)_2$ | 3 | $-\underset{F}{\overset{}{CH}}-CH_2-$ | C₄H₉ |
| 182. | 2 | CH=CH | (CH₂)₅ | $\overset{O}{\underset{}{\overset{\|}{C}}}NHC_6H_5$ | 4 | $-\underset{F}{\overset{F}{C}}-CH_2$ | —(CH₂)₂CH=CHCH₃ |
| 183. | 3 | (CH₂)₂ | $-\underset{CH_3}{\overset{}{CH}}-\underset{F}{\overset{}{CH}}-$ | CH₂OH | 1 | (CH₂)₂ | C₆H₅ |
| 184. | 4 | (CH₂)₂ | (CH₂)₂ | (tetrazolyl) | 2 | CH₂ | —CH₂C₆H₅ |
| 185. | 1 | CH=CH | (CH₂)₃ | CO₂CH₃ | 3 | (CH₂)₃ | —C₆H₄—p-(CH₂)₂—CH₃ |
| 186. | 2 | (CH₂)₂ | (CH₂)₄ | CO₂CH₃ | 4 | (CH₂)₈ | C₆H₅ |
| 187. | 3 | CH=CH | (CH₂)₅ | CO₂H | 1 | (CH₂)₁₀ | C₆H₄p-CH₂CH₃ |

What is claimed is:

1. A compound having the structure

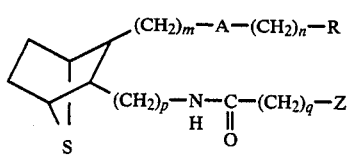

including all stereoisomers thereof, wherein m is ; n is 1 to 5; R is CO₂H, CO₂alkyl, CO₂ alkali metal, CO₂ polyhydroxyamine salt,

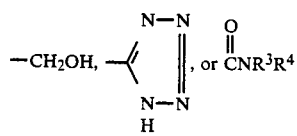

wherein R³ and R⁴ are the same or different and are H, lower alkyl, hydroxy, lower alkoxy or aryl, at least one of R³ and R⁴ being other than hydroxy and lower alkoxy; p is 1 to 4; Z is

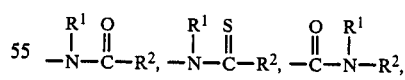

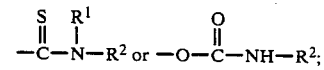

q is 1 to 12; R¹ is H or lower alkyl; and R² is H, lower alkyl, lower alkenyl, lower alkynyl, aryl, arylalkyl, lower alkoxy, arylalkoxy, aryloxy, amino, alkylamino, arylamino, arylalkylamino,

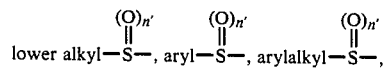

-continued

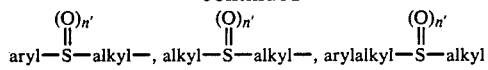

(wherein n' is 0, 1 or 2), alkylaminoalkyl, arylaminoalkyl, arylalkylaminoalkyl, alkoxyalkyl, aryloxyalkyl or arylalkoxyalkyl, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

cycloalkyl alone or as part of another group is a saturated cyclic hydrocarbon group containing 3 to 12 carbons, which is unsubstituted or substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonyl amino groups, 1 or 2 amino groups, 1 or 2 nitro groups, 1 or 2 cyano groups, 1 or 2 thiol groups and/or 1 or 2 alkylthio groups; and aryl alone or as part of another group is a monocyclic or bicyclic aromatic group containing 6 to 10 carbons in the ring portion and which is unsubstituted or is substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defind in claim 1 having the structure

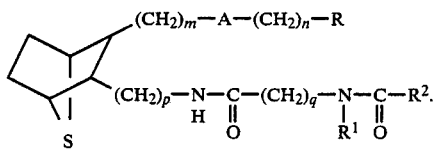

3. The compound as defined in claim 1 having the structure

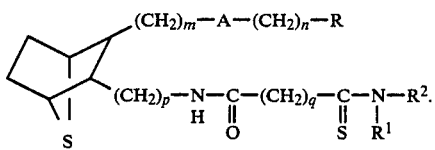

4. The compound as defined in claim 1 having the structure

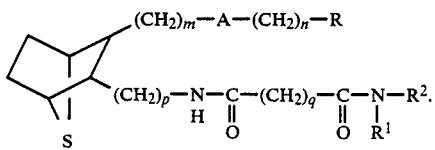

5. The compound as defined in claim 1 having the structure

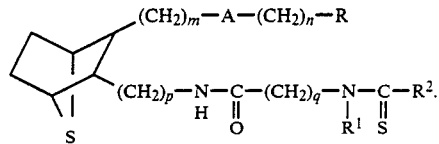

6. The compound as defined in claim 1 having the structure

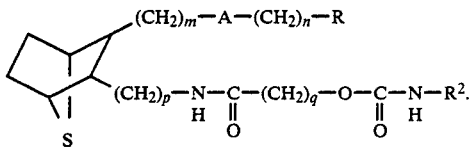

7. The compound as defined in claim 1 wherein $R^1$ is H and $R^2$ is alkyl, alkoxy or arylthioalkyl.

8. The compound as defined in claim 1 wherein A is CH=CH.

9. The compound as defined in claim 1 wherein m is 1 and n is 1 to 4.

10. The compound as defined in claim 1 wherein p is 1 and q is 1.

11. The compound as defined in claim 1 wherein R is $CO_2$ alkyl or $CO_2H$.

12. The compound as defined in claim 1 wherein $R^1$ is H and $R^2$ is H or $CH_3$.

13. The compound as defined in claim 1 having the name [1β,2α(5Z),3α,4β]-7-[3-[[[[(1-oxohexyl)amino]acetyl]amino]methyl]-7-thiabicyclo[2.2.1]hept-2-yl]-5-heptenoic acid or esters thereof, including all stereoisomers thereof.

14. The compound as defined in claim 1 having the name [1β,2α(5Z),3α,4β]-7-[3-[[[[(butylamino)carbonyl]amino]acetyl]amino]methyl]-7-thiabicyclo[2.2.1-]hept-2-yl]-5-heptenoic acid or esters thereof, including all stereoisomers thereof.

15. The compound as defined in claim 1 having the name [1β,2α(5Z),3α,4β]-7-[3-[[[[methyl(1-oxohexyl)amino]acetyl]amino]methyl]-7-thiabicyclo[2.2.1]hept-2-yl]-5-heptenoic acid or esters thereof, including all stereoisomers thereof.

16. The compound as defined in claim 1 having the name [1β,2α(5Z),3α,4β]-7-[3-[[[[(butoxycarbonyl)amino]acetyl]amino]methyl]-7-thiabicyclo[2.2.1]hept-2-yl]-5-heptenoic acid or esters thereof, including all stereoisomers thereof.

17. The compound as defined in claim 1 having the name [1β,2α(5Z),3α(R),4β]-7-[3-[[[1-oxo-2-[(1-oxohexyl)amino]propyl]amino]methyl]-7-thiabicyclo[2.2.1-]hept-2-yl]-5-heptenoic acid or esters thereof, including all stereoisomers thereof.

18. The compound as defined in claim 1 having the name [1β,2α(5Z),3α(S),4β]-7-[3-[[[1-Oxo-2-[(1-oxohexyl)amino]propyl]amino]methyl]-7-thiabicyclo[2.2.1-]hept-2-yl]-5-heptenoic acid or esters thereof, including all stereoisomers thereof.

19. The compound as defined in claim 1 having the name [1β,2α(5Z),3α,4β]-7-[3-[[[[(1-oxo-4-phenyl)butyl]amino]acetyl]amino]methyl]-7-thiabicyclo[2.2.1]hept-2-yl]-5-heptenoic acid or esters thereof including all stereoisomers thereof.

20. The compound as defined in claim 1 having the name [1α,2β(Z),3β,4α]-7-[3-[[[[(phenylthio)acetyl- ]amino]acetyl]amino]methyl]-7-thiabicyclo[2.2.1]hept-2-yl]-5-heptenoic acid or esters thereof including all stereoisomers thereof.

21. The compound as defined in claim 1 having the name [1α,2β(Z),3β,4α]-7-[3-[[[[[3-(4-hydroxyphenyl)-1-oxopropyl]amino]acetyl]amino]methyl]-7-thiabicyclo[2.2.1]hept-2-yl]-5-heptenoic acid or esters thereof including all stereoisomers thereof.

22. The compound as defined in claim 1 having the name [1α,2β(Z),3β,4α]-7-[3-[[[[(phenoxyacetyl)amino]acetyl]amino]methyl]-7-thiabicyclo[2.2.1]hept-2-yl]-5-heptenoic acid or esters thereof including all stereoisomers thereof.

23. The compound as defined in claim 1 having the name [1α,2β(5Z),3β,4α]-7-[3-[[[[(1-oxo-3-phenylpropyl)amino]acetyl]amino]methyl]-7-thiabicyclo[2.2.1]hept-2-yl]-5-heptenoic acid or esters thereof including all stereoisomers thereof.

24. The compound as defined in claim 1 having the name [1α,2β(5Z),3β,4α]-7-[3-[[[(1-oxo-5-phenylpentyl)amino]acetyl]amino]methyl]-7-thiabicyclo[2.2.1]hept-2-yl]-5-heptenoic acid or esters thereof including all stereoisomers thereof.

25. The compound as defined in claim 1 having the name [1α,2β(Z),3β,4α]-7-[3-[[[[(4-cyclohexyl-1-oxobutyl)amino]acetyl]amino]methyl]-7-thiabicyclo[2.2.1]hept-2-yl]-5-heptenoic acid or esters thereof including all stereoisomers thereof.

26. The compound as defined in claim 1 having the name [1α,2β(Z),3β,4α]-7-[3-[[[[[1-oxo-3-(phenylthio)propyl]amino]acetyl]amino]methyl]-7-thiabicyclo[2.2.1]hept-2-yl]-5-heptenoic acid or esters thereof including all stereoisomers thereof.

27. The compound as defined in claim 1 having the name [1α,2β(Z),3β,4α]-7-[3-[[[[[(phenylmethyl)thio]acetyl]amino]acetyl]amino]methyl]-7-thiabicyclo[2.2.1]hept-2-yl]-5-heptenoic acid or esters thereof including all stereoisomers thereof.

28. The compound as defined in claim 1 having the name [1α,2β(Z),3β,4α]-7-[3-[[[[[(butylthio)acetyl]amino]acetyl]amino]methyl]-7-thiabicyclo[2.2.1]hept-2-yl]-5-heptenoic acid or esters thereof including all stereoisomers thereof.

29. The compound as defined in claim 1 having the name [1α,2β(Z),3β,4α]-7-[3-[[[[[(cyclohexylmethyl)thio]acetyl]amino]acetyl]amino]methyl]-7-thiabicyclo[2.2.1]hept-2-yl]-5-heptenoic acid or esters thereof including all stereoisomers thereof.

30. The compound as defined in claim 1 having the name [1α,2β(Z),3β,4α]-7-[3-[[[[(phenylsulfinyl)acetyl]amino]acetyl]amino]methyl]-7-thiabicyclo[2.2.1]hept-2-yl]-5-heptenoic acid or esters thereof including all stereoisomers thereof.

31. The compound as defined in claim 1 having the name [1α,2β(Z),3β,4α]-7-[3-[[[[(phenylsulfonyl)acetyl]amino]acetyl]amino]methyl]-7-thiabicyclo[2.2.1]hept-2-yl]-5-heptenoic acid or esters thereof including all stereoisomers thereof.

32. A method of inhibiting platelet aggregation and/or bronchoconstriction which comprises administering to the circulatory system of a mammalian host an effective amount of a compound as defined in claim 1 or a pharmaceutically acceptable salt thereof.

33. The method as defined in claim 32 wherein said compound is administered in an amount within the range of from about 1 to about 100 mg/kg.

34. A composition for inhibiting platelet aggregation and/or bronchoconstriction comprising an effective amount of a compound as defined in claim 1 or a pharmaceutically acceptable salt thereof, and a pharmaceutically acceptable carrier therefor.

35. A method of treating peripheral vascular diseases, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,735,962

DATED : April 5, 1988

INVENTOR(S) : Masami Nakane

It is certified that error appears in the above-identified patent and that said Letters Patent is hereby corrected as shown below:

Column 81, line 59, after "m is", insert --1 to 4; A is -CH=CH- or -CH$_2$-CH$_2$- --.

Signed and Sealed this

Twenty-third Day of August, 1988

Attest:

DONALD J. QUIGG

Attesting Officer

Commissioner of Patents and Trademarks